United States Patent
Drinan et al.

(10) Patent No.: US 7,044,911 B2
(45) Date of Patent: May 16, 2006

(54) GATEWAY PLATFORM FOR BIOLOGICAL MONITORING AND DELIVERY OF THERAPEUTIC COMPOUNDS

(75) Inventors: Darrel Drinan, San Diego, CA (US); Carl F. Edman, San Diego, CA (US); Diethard Merz, San Diego, CA (US)

(73) Assignee: PhiloMetron, Inc., San Diego, CA (US)

( * ) Notice: Subject to any disclaimer, the term of this patent is extended or adjusted under 35 U.S.C. 154(b) by 68 days.

(21) Appl. No.: 10/032,765

(22) Filed: Oct. 29, 2001

(65) Prior Publication Data

US 2003/0004403 A1    Jan. 2, 2003

Related U.S. Application Data

(60) Provisional application No. 60/301,897, filed on Jun. 29, 2001.

(51) Int. Cl.
*A61B 5/00* (2006.01)

(52) U.S. Cl. .................. 600/300; 128/903; 128/904; 604/174; 604/65

(58) Field of Classification Search ........ 600/300–301, 600/345, 347, 361, 365; 128/903–905, 920; 705/2, 3; 604/174, 175, 290, 65–68; 607/28–32, 607/58–60
See application file for complete search history.

(56) References Cited

U.S. PATENT DOCUMENTS

| | | | |
|---|---|---|---|
| 4,402,694 A * | 9/1983 | Ash et al. ............... | 604/891.1 |
| 4,854,328 A | 8/1989 | Pollack | |
| 5,242,415 A * | 9/1993 | Kantrowitz et al. ........ | 604/175 |
| 5,375,604 A | 12/1994 | Kelly et al. | |
| 5,445,008 A | 8/1995 | Wachter et al. | |
| 5,511,553 A | 4/1996 | Segalowitz | |
| 5,558,638 A | 9/1996 | Evers et al. | |
| 5,752,976 A | 5/1998 | Duffin et al. | |
| 5,779,630 A | 7/1998 | Fein et al. | |
| 5,833,603 A | 11/1998 | Kovacs et al. | |
| 5,987,352 A | 11/1999 | Klein et al. | |
| 6,016,686 A | 1/2000 | Thundat | |
| 6,083,248 A | 7/2000 | Thompson | |
| 6,092,530 A | 7/2000 | Weissman et al. | |
| 6,175,752 B1 | 1/2001 | Say et al. | |

(Continued)

FOREIGN PATENT DOCUMENTS

WO    WO 98/40009    9/1998

(Continued)

OTHER PUBLICATIONS

Samarati et al, Data Security, Wiley Encyclopedia of Electrical and Electronics Engineering Online, Dec. 1999.*

*Primary Examiner*—Max F. Hindenburg
*Assistant Examiner*—Michael C. Astorino
(74) *Attorney, Agent, or Firm*—Knobbe Martens Olson & Bear LLP

(57) ABSTRACT

The invention relates to methods and devices for remote or distributed continuous monitoring of physiologically relevant states. The invention provides for methods to automatically detect deviations or other states in physiological parameters and automatically alert a measured subject, user or other authorized party. The device provides for a universal platform for sensors, and further provides for the automatic compensation or distribution of devices or bioactive agents at appropriate levels and/or intervals in response to deviations or other states sensed in various physiological parameters.

12 Claims, 9 Drawing Sheets

U.S. PATENT DOCUMENTS

| | | |
|---|---|---|
| 6,198,394 B1 * | 3/2001 | Jacobsen et al. ............ 600/301 |
| 6,213,942 B1 | 4/2001 | Flach |
| 6,225,901 B1 | 5/2001 | Kail |
| 6,287,252 B1 | 9/2001 | Lugo |
| 6,360,888 B1 * | 3/2002 | McIvor et al. .............. 600/345 |
| 6,459,917 B1 * | 10/2002 | Gowda et al. .............. 600/576 |
| 6,540,672 B1 * | 4/2003 | Simonsen et al. .......... 600/300 |
| 6,645,142 B1 * | 11/2003 | Braig et al. ................. 600/300 |

FOREIGN PATENT DOCUMENTS

| | | |
|---|---|---|
| WO | WO 00/54237 | 9/2000 |
| WO | WO01/37726 A1 | 5/2001 |

* cited by examiner

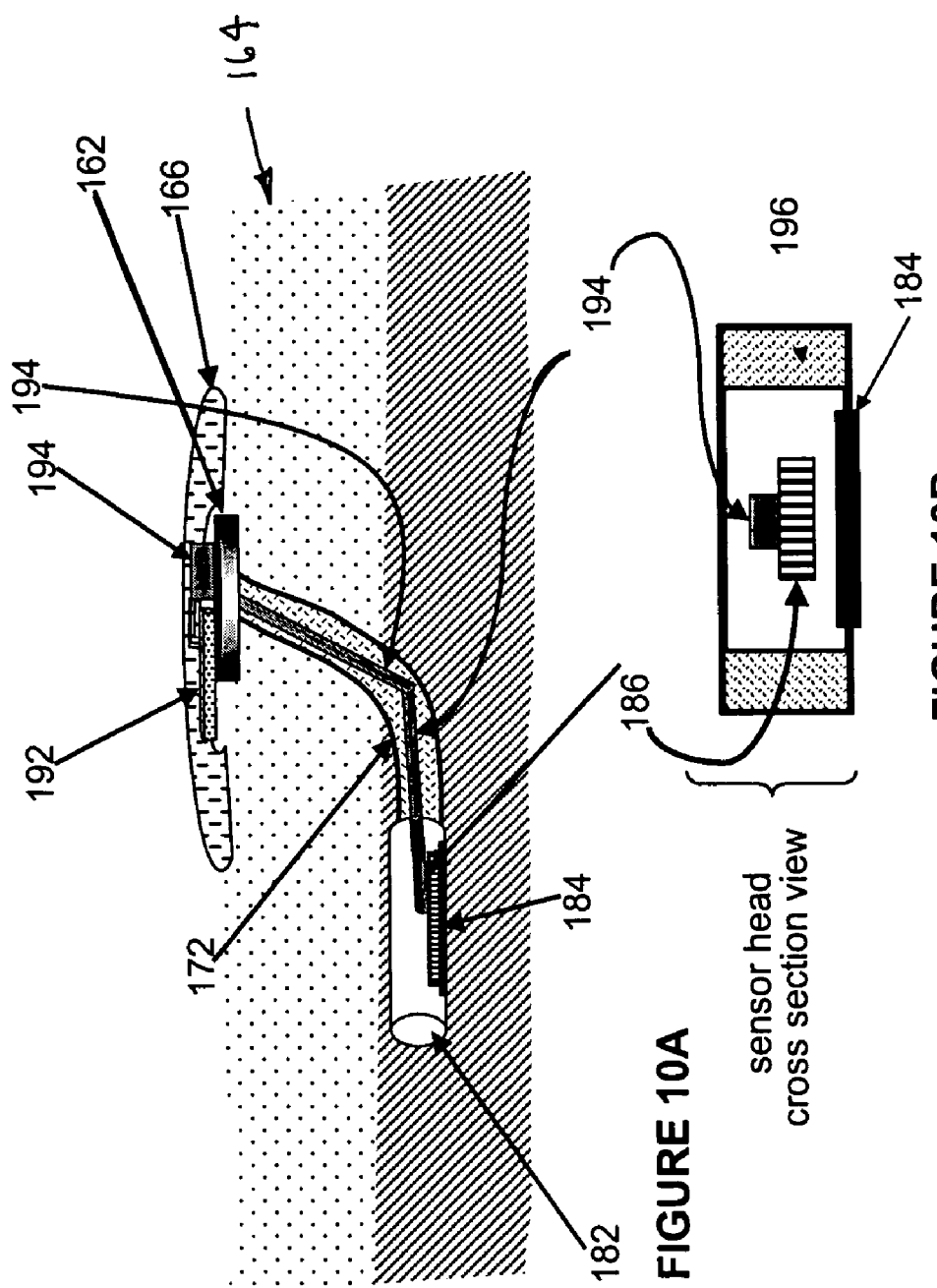

Bio Interface Head
- Interact with Body in order to derive a technically measurable signal
- Generate electrical signal
- Condition the electrical signal
- Filter
- Encode

FIGURE 11

Control & Communication Module
- Dynamic Signal Pre-Processing:
- A/D conversion
- Signal Conditioning (Noise reduction, Amplification, Averaging...)
- Error Diagnosis
- Error correction
- ID management
- Sensor Type
- Serial Number
- Communication to DCU
- Transmit and Receive Data
- Encryption
- Transmission Protocol
- Time Reference
- Power Supply, also for BIH
- Power Control
- Feedback device

FIGURE 12

Data Collection Unit
- Communication to CCM
- Data processing
- Input device, Display and Actuators as user interface
- Network interface
- Power Supply

FIGURE 13

GATEWAY PLATFORM FOR BIOLOGICAL MONITORING AND DELIVERY OF THERAPEUTIC COMPOUNDS

CROSS-REFERENCE TO RELATED APPLICATIONS

This application claims the benefit of U.S. Provisional Application Ser. No. 60/301,897, filed Jun. 29, 2001.

FIELD OF THE INVENTION

This invention relates to methods and devices for remote or distributed monitoring of physiological states. The invention provides for methods to detect deviations in physiological parameters through the establishment of baseline values, either by direct inspection of compiled data or by computer aided analysis. The device provides for a universal platform for sensors, which may also allow automatic compensation or distribution of devices or bioactive agents at appropriate levels and/or intervals in response to deviations sensed in various physiological parameters.

BACKGROUND OF THE INVENTION

Long-term monitoring of physiological parameters has been particularly problematic to implement. This type of monitoring may be essential in many situations, especially for patients that exhibit transitory physiological abnormalities. The implementation of long-term monitoring can help solve several problems for at-risk patient care such as: 1) allows continuous monitoring, alerting care givers and patients to potential problems while patients are away from a managed care setting; 2) allows true baselines to be obtained, making deviations easier to detect; and 3) allows the automatic collection of important data necessary to determine the efficacy or non-efficacy of therapeutic treatments.

Long-term monitoring is typically easier to accomplish for non-ambulatory patients. There are many examples of devices that monitor physiological parameters in a hospital setting such as electrocardiograms, electroencephalograms, pulse, heart rate, blood pressure, and so on. However, for individuals that lead an active life, very few options presently exist for long-term monitoring of physiological conditions. Most devices only measure periodically and are prone to measurement variations caused by technique, compliance or use. Most often, these devices require a professional to operate and monitor the condition of the device, as well as to assure patient compliance in order to maintain proper functioning of the monitoring instrument. In addition, biocompatibility issues with many of these external devices are numerous, with side effects such as attendant skin irritations, increasing patient non-compliance with the monitoring devices.

Invasive devices can also introduce complications. Although non-compliance and measurement variation issues may be decreased with semi-permanent implantable sensors, biocompatibility issues are even higher. Implantable devices often have a shortened half-life, due to rejection of the device in the patient, accumulation of biological materials on the device themselves or other events, including infection and mechanical breakdown of the device. U.S. Pat. No. 6,092,530 provides a sensor on the implantable device, which monitors accumulation of biological material on the sensor itself, decreasing the need to investigate the state of the device through invasive measures. The sensor is remotely interrogated by an external device via electromagnetic or high-frequency radio waves, triggering the sensor to transmit encoded data to the external reader device.

Other medical sensors have been described which measure various physiological parameters for remote monitoring. For example, U.S. Pat. No. 5,987,352 to Klein, et al. discloses a minimally invasive implant coupled with a telemetry system that stores triggered electrocardiogram data. This device records physiological events that meet a set threshold parameter, which is subsequently downloaded to an external reader device through external interrogation. U.S. Pat. No. 5,833,603 to Kovacs et al. provides a device for monitoring various physiological parameters and storing identified data. Similarly, U.S. Pat. No. 4,854,328 to Pollack discloses an animal monitoring system, which comprises an implantable temperature sensor, and transmitter, which transmits a signal, upon sensing a predetermined threshold value, to a remote receiver. Because the devices record only data that satisfies a set threshold parameter, it is unsuitable for establishing baseline patterns necessary in detecting low frequency events. Both devices also require an external interrogator device, which prompts the transponder to download collected data to an external recording device.

Other wireless technologies enable measurement of various physiological parameters on externally-based or implanted biosensors. U.S. Pat. No. 5,511,553 to Segalowitz also discloses a device which measures multiple electrophysiological parameters that provide continuous monitoring in a wireless fashion for assessment of cardiovascular condition in ambulatory patients. U.S. Pat. No. 6,175,752 to Say et al. discloses an analyte monitor which measures multiple physiological parameters and provides for continuous monitoring in a wireless fashion. The device also provides for a drug-delivery system to alter the level of the analyte based on the data obtained using the sensor. Although both devices combine the use of biological sensors with wireless transmission of data, it does not appear that they provide for a long-lasting, biologically compatible system that allows continuous feedback and analysis with a network-based system capable of relaying information from remote sensors on a mammlian subject to a central data analysis system. There exists a continuing need for long-term physiological monitoring devices that provide sensors which reduce biocompatibility issues and provides a wireless data-relay system which reliably transmits bioparameter data, allowing continuous or periodic monitoring of a patient's or users physiological state.

SUMMARY OF THE INVENTION

Accordingly, one aspect of the present invention is to address the shortcomings mentioned above by providing for methods and devices which allow the continuous or periodic monitoring of physiological conditions. Physiological parameters are monitored via sensors mounted within a BioInterface Head (BIH), which is linked to a Communication and Control Module (CCM). The CCM controls the BIH function and automatically transmits converted and encrypted information to a Data Collection Unit (DCU) via remote telemetry. The information from the DCU is analyzed and may be forwarded to a remote data management system which will allow access by the measured subject, caregiver or other authorized individuals by remote telemetry or other forms of communication (FIG. 1). An automatic compensation delivery mechanism may also be incorporated into the device, which may deliver therapeutic agents, compounds or other materials in response to detected abnormalities or fluctuations in various physiological parameters, or to outside authorized command.

One aspect of this invention is a device which automatically and continuously or periodically monitors physiological conditions in vivo using surface or sub-surface implanted sensors linked to CCM's and DCU's. By continuously monitoring physiological parameters remotely or in a distributed environment, baseline or reference data can be obtained, allowing detection of deviations in measured subjects. The device particularly distinguishes itself from long-term monitoring devices currently available by: 1) improving measured data quality by diminishing data variation caused by the user, technique or compliance issues; 2) converting, encrypting and identifying data for further transmission and processing of data; 3) incorporating a wireless transmission signal system (e.g. radio frequency, acoustic or optical) or other remote communication method to allow automatic transmission of data collected from the CCM/BIH assembly to either adjacent or remote CCM's or DCU's; 4) reducing biocompatibility issues associated with implantable sensors with the use of novel biomaterials and devices to decrease the adhesion or encapsulation of the biofluid access port by biological processes; and 5) coupling the wireless signal system to enable a two-way wireless-based control system to allow controlled or automatic delivery of compounds or devices from the CCM/BIH assembly.

In one aspect, the BIH assembly may comprise various types of sensing mechanisms, including thermal sensors (thermoresistors, thermocouples), electrical sensors (EKG, ECG, impedance, frequency or capacitance), optical sensors (photonic wavelength, colorimetric, turbidity), chemical sensors (pH, biomolecules, gases such as $CO_2$, and other chemical sensors), enzyme-linked sensors (glucose oxidase, phosphatase, coupled substrates (e.g. horseradish peroxidase or alkaline phosphatase and other enzyme-linked sensors)), radiation sensors (gamma, beta and other radiation detectors), magnetic sensors (micro NMR circuitry and magnetic spin state) and physical sensors, such as flow meters and pressure sensors. Alternatively, the sensor may also comprise a MEMS (Micro Electrical Mechanical Systems) or a MOEMS (Micro Optical Electrical Mechanical Systems) sensing device, comprising at least one cantilever beam coated with polymeric compounds for detection of various physiological substances or conditions. The microcantilever beams allow increases in sensitivity and specificity, as compared to currently available technologies, and simplifies detection by coupling the beam to transducers which measure changes in capacitance, resonant frequency, or other techniques used in detecting mass changes in the spring element of the cantilever beam. In still other embodiments, nanotechnology devices may be incorporated into the sensor head or other components of the device for more accurate detection, cellular manipulation and measurement of physiological parameters. In one embodiment the BIH assembly, as well as other components of the system, may contain components micron, submicron or nanoscale in dimension, further lessening the obtrusiveness of the device to wearer.

In another aspect, the BIH assembly of the sensor element comprises materials that permit interaction of the sensor with the host environment. This includes microchannels, gel, fine mesh, screen, membrane, filters or a microporous frit, which permit interaction of sensors to the host environment while maintaining a segregated and sterile environment within the sensing element itself. This tends to extend the life of the sensor by preventing fouling of the biological sensor with macromolecules and other substances that can adhere onto the sensor mechanism.

In accordance with another aspect of the invention, the use of specialized biomedia can be incorporated into the sensing head device and may decrease the exposure of the sensor element to the external environment. This biomedia system may also decrease the adherence of the sensor element onto the host tissue or layer, a large component of the rejection mechanism of biological sensors. Moreover, the use of a biomedia system may lower trauma to the surrounding tissue or layer by providing medium that is physiologically compatible with the host, mimicking the tissue environment in which the sensor is implanted. In yet another aspect of the invention, growth factors, cell signaling and cell adhesion molecules will be integrated into the biomedia system, mimicking the tissue and further improving biocompatibility issues of the sensor implantation into the host species.

In other aspects, the biomedia may have gel-like properties at ambient room temperature, whereupon exposure to higher body temperatures changes the material to a fluid-like state and becomes less viscous. One utility of this gel-like material may be its use as part of a calibration process for the sensor elements. When the sensor is implanted on or into the host, the sensor itself is shielded from the host environment by the gel-like material. As the temperature around the sensor increases, the gel-like material changes viscosity, freeing calibration molecules from the matrix that then enter into the sensor. The sensor can then be accurately calibrated before being equilibrated into the host environment. The bio-media may also be used as a process or method during manufacturing. The bio-media may also provide increased product shelf-life storage by insulating the sensors on the BIH from degradation caused by ambient conditions such as temperature, humidity or other degenerative storage issues.

In another aspect of the invention, the BIH assembly, located on top or within the dermal layer, interacts with the CCM (Control and Communication Module) that is also located on top or within the dermal layer. The CCM interacts with the sensor unit either directly through a physical means (e.g. conductive wire, optical, acoustic or other means) or indirectly using a remote wireless-based signal and control system. The CCM also contains a power supply consisting of either a removable or responder power source. The CCM and the BIH assembly, if located on top of the dermal layer, are attached to the host patient through a bioadherence system, which allows minimal irritation of the outer body surface, thereby tending to decrease rejection and increase the longevity of the BIH and CCM assemblies.

In one particular aspect of the invention, the BIH is monitored externally by direct communication with the CCM. The CCM can automatically, and continually or periodically, download stored converted and encrypted information to a Data Collection Unit (DCU). The CCM may also automatically, and continually or periodically, download stored information to a remote or adjacent CCM in areas where signal transmission may be problematic. Where communication between the CCM and DCU is possible, but not between the DCU and the remote database management system, the DCU may download information to another remote or distributed DCU until communication linkage with the remote database management system can be established. The CCM is also capable of receiving processed information from a remote database management system, DCU or adjacent or remote CCM, alerting the patient or user through a separate communication channel or method, such as through a localized display (e.g. visual, physical or acoustic means (liquid crystal display, organic light emitting diode (OLED) display, magnetically sensitive liquid ink displays, audio alarm, physical vibrations or paging mechanism)), or telecommunications pathway.

According to another aspect of the invention, the Bio Interface Head (BIH) comprises a release system delivering therapeutic agents, which are administered in response to detected changes in various physiological parameters. The release system contained within the BIH interacts with the CCM and releases therapeutic agents in response to instructions received from the CCM. The CCM can be programmed to directly trigger delivery of therapeutic agents, or can be coupled to an external control circuitry, allowing remote monitoring of a patient's condition and subsequent adjustment of therapeutic agents in order to stabilize various physiological indicators.

While the advantages and features of the invention have been described above, a detailed description of the invention can be found below with accompanying embodiments. These embodiments are illustrative of the many ways in which this invention can be exploited, and further advantages and features will become apparent through the detailed description of the invention and their accompanying drawings.

BRIEF DESCRIPTION OF THE DRAWINGS

These and other objects, advantages and features of the present invention will be more readily understood from the following detailed description of the preferred embodiments thereof, when considered in conjunction with the following drawings.

FIG. 11. General requirements for electronics in BIH

FIG. 12. General requirements for electronics in CCM

FIG. 13. General requirements for electronics in DCU

DEFINITIONS

Figure 1:
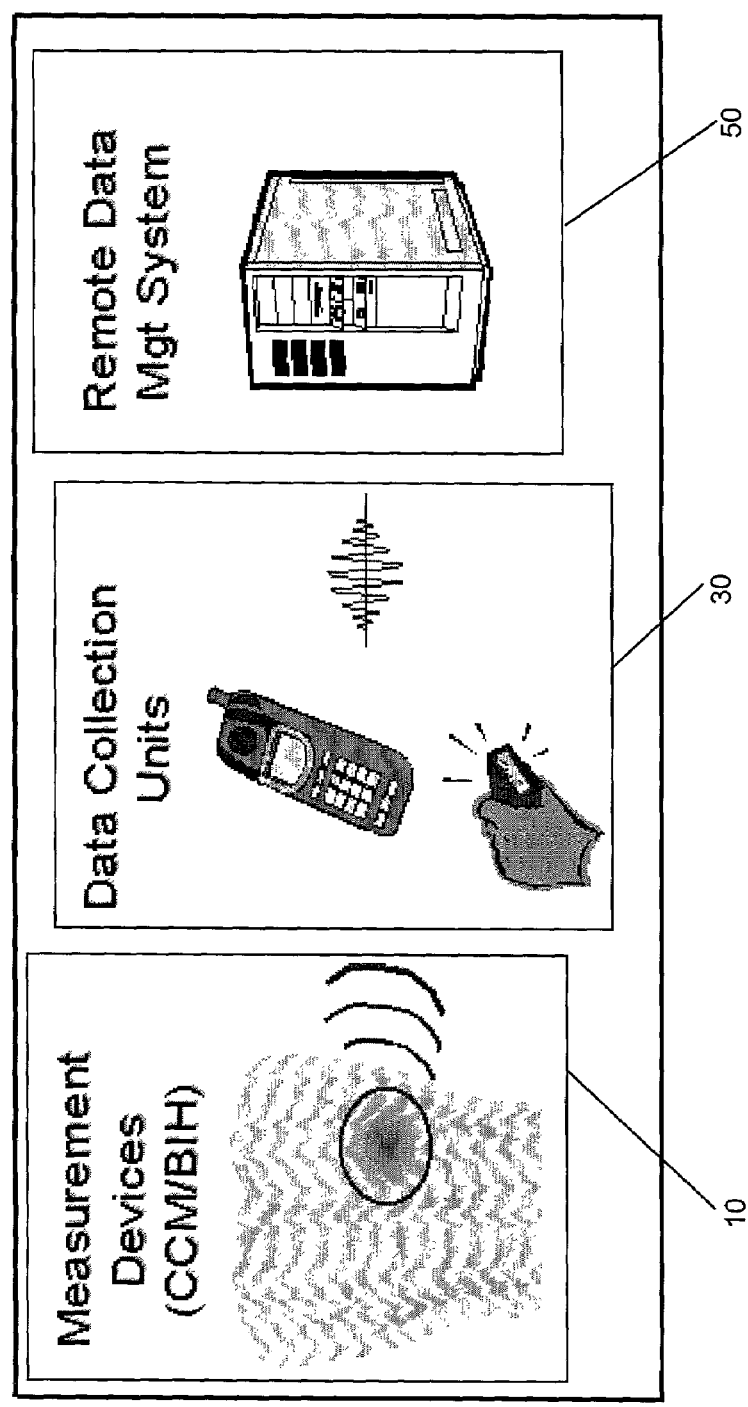
FIG. 1. Components of the Human Gateway System.

HUMAN GATEWAY (HG) Platform—This describes a system of components, devices, data management systems and services necessary to remotely measure bioparameters, collect the data in a wireless remote environment, analyze and summarize the data and provide access to this data by the mammalian subject, clinician or authorized third party. In addition it may include a two-way secure communication system enabling a mammalian subject and clinician to remotely communicate diagnostic knowledge and/or actions.

BIH—BioInterface Head. May include sensors, interface or sensor mounting features, data communication features, and structures for limiting movement or ensuring placement on the measured subject of the sensors.

CCM—Control and Communication Module. Contains circuitry and means necessary to receive signals from the BIH, other CCM's and DCU, process those signals and/or transmit them to a DCU, BIH or another CCM.

DCU—Data Collection Unit. Contains circuitry and means necessary to receive and send signals from at least one CCM, DCU or external transmissions from other telemetry systems e.g. cellular, pager, fixed telemetry or other telemetry systems.

Biomedia—Specialized medium to decrease exposure of the sensor element to the external environment. Biomedia may consist of material that is biologically and physiologically compatible with the host patient, whereby the properties are such that external calibration standards or markers are incorporated into the device and are released upon insertion of the device into the host patient. Biomedia may consist of any physiologically compatible reagent including, but not limited to: hydrogels, agarose, gelatin, starches, or any other natural or artificial polymeric compound.

Body surface—Body surfaces covered by epidermis or other related cell types and exposed to the external environment, either continually or transiently without piercing or otherwise penetrating the integrity of this surface. Examples of these surfaces include but are not limited to: skin or internal surfaces such as the mucosal surfaces that are found in the mouth, nasal passages, or other body passages.

Conditioned Data—data received from the BIH and processed to remove extraneous noise or signals, as well as other procedures for enhancing signal quality and transmission.

Continuously—Application-dependent frequency of measurement not requiring user intervention.

Database Management System—Computer-based management system for processing, storing and summarization of sensor data to determine physiological parameters of the mammalian subject, detect deviations or abnormalities in the physiological parameters, determine the mode of action in response to an analysis of the physiological parameters or any other analysis and processing of the data necessary in evaluation of the mammalian subject. Control instructions in response to the processed data may be transmitted back to the mammalian subject or other authorized personnel through a computer-based or wireless communications means.

Data Transmission Device—personal digital assistant, pagers or other devices capable of data transmission or receiving information or instructions.

Encrypted Data—asymmetric or symmetric encryption of data received from sensors into encrypted text. Allows the transmission of data and subsequent receipt of the same to be performed on any available control and communication module or data collection unit.

Mammalian Subject—the human, animal or other organism in which measurements are being collected.

Periodically—User or system-controlled measured frequency.

Processed Data—error diagnosis and/or correction and analog to digital conversion or digital to analog conversion, as well as other means for enabling or enhancing the transmission of data.

Remotely located—not in physical connection to mammalian subject.

Subdermally—located beneath the dermal layer surface.

Subcutaneously—located beneath the skin surface.

Sensor—Mechanical, electrical or optical sensing devices that measure information such as physiologically relevant information (e.g. temperature, pressure, EKG, ECG, pH, biochemicals, biomolecules, gases such as $CO_2$, and other chemical parameters, enzyme-based parameters, radiation, magnetic and physical parameters, such as blood flow, blood pressure or other physical parameters), or other information (e.g. body positioning, GPS location).

Wireless means—radio frequency, acoustic or optical means for transmitting and receiving information.

DETAILED DESCRIPTION OF THE INVENTION

The devices and methodologies of this invention provide a platform for the mounting of biosensor modules useful for the monitoring of bio-parameters including, but not limited to: physical measurements; e.g. temperature, motion, electrical, conductivity and pressure; (Wheatstone bridge measurements), chemical measurements, e.g. concentration of salts, drugs, metabolites, hormones, and pH; and bioactive assays, e.g. testing for the presence or absence of antibodies, or other biomolecules or bioactivities from within the mammalian subject. Once obtained, these data are transmitted from the BIH components to the CCM for compilation and response. Overall the device can be designated as a HUMAN GATEWAY (HG) platform (FIG. 1). It is a unique feature of this invention that the data collection is automatic, autonomous and unobtrusive. In addition, it may be linked to a two-way communication system, remote storage or data analysis system.

It is another unique feature of this invention that it may serve as a platform onto which one or more sensors can be incorporated as needed and as sensor systems change. That is, it is a feature of the invention that the HG (HUMAN GATEWAY) platform provides the basic infrastructure for a universal bioparameter monitoring platform. Another feature of the invention is that the device may also serve to provide metered release of devices or delivery of suitable agents (e.g. therapeutics) to the body through suitable components incorporated within the BIH. This invention features a linkage between the BIH, containing at least one sensor module, CCM, and a remote DCU by use of a data relay system utilizing a wireless-based data transmission system (e.g. RF, acoustic or optical). This wireless-based system may be used to relay biometric data and control signals from the BIH to the CCM as well as to and from the data collection unit (DCU).

In a preferred embodiment of the invention (FIG. 1), the HG is comprised of three principle components. The first component 10 comprises the BioInterface Head (BIH) and Control and Communication Module (CCM). The second component 30 is the Data Collection Unit (DCU), and the third component 50 is the Database Management System. The CCM and DCU components function to relay both bio-parameter measurements and signals to and from sensor modules mounted or otherwise attached to the BIH, which may be attached to the CCM.

Figure 2:
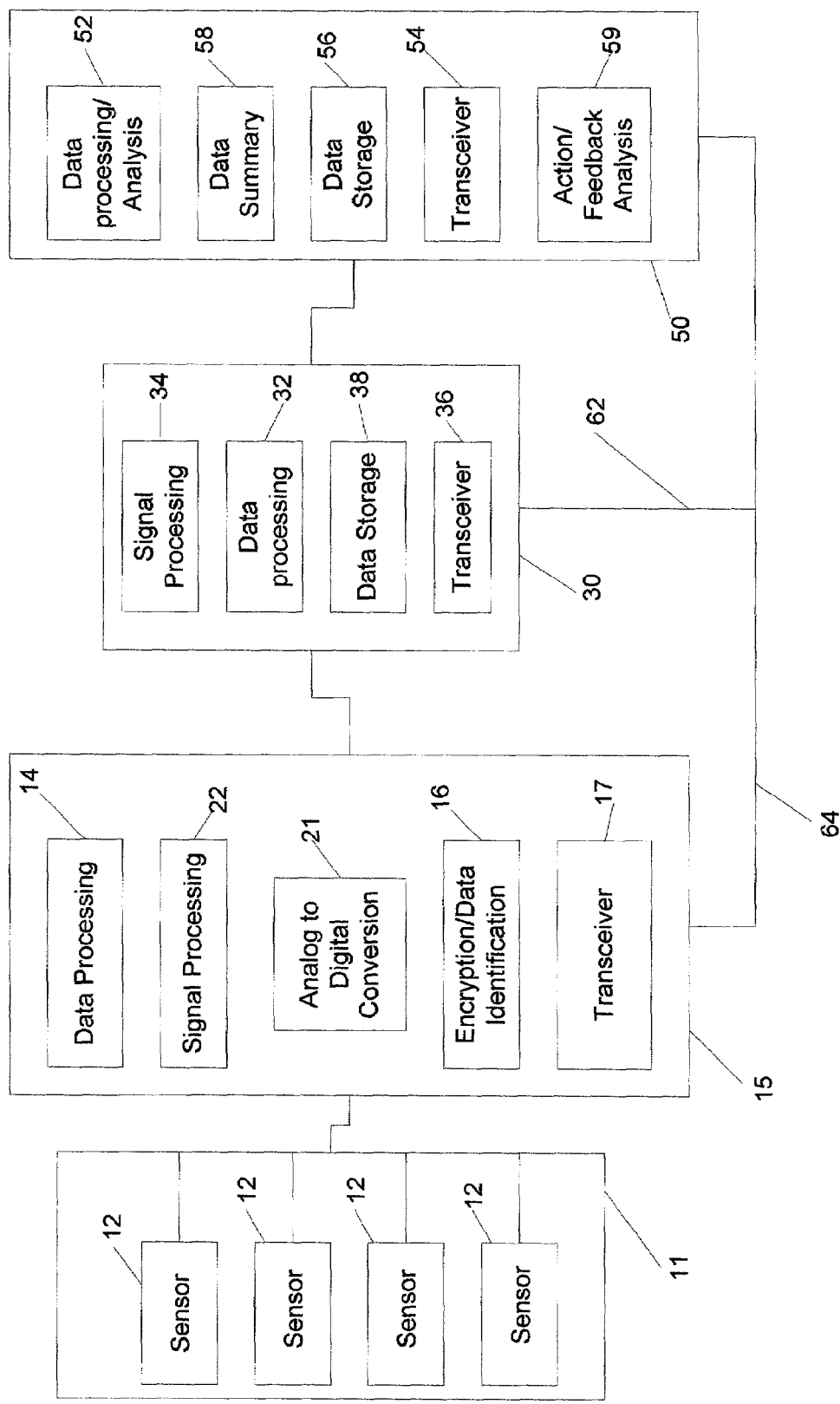
FIG. 2. Block level diagram of an embodiment of the system, wherein sensor information from the BIH is preliminarily processed by the CCM and transmitted to the DCU and remote database management system. The remote database management system, based on information received by the sensor, is capable of providing feedback analysis to the DCU or CCM or both.

In operation (FIG. 2), the BIH 11 obtains bioparameter data from sensor 12 measuring appropriate bodily conditions, states or composition, e.g. temperature, pH, or levels of defined biomolecules. The BIH 11 then communicates this data to the CCM 15. The CCM contains optimized circuitry necessary for basic data processing 14, signal processing 22, and data transmission 17. The CCM 15 relays the data stream to an adjacent DCU 30 unit. The DCU 30 units may be fixed at defined locations (e.g. fixed intervals in building corridors) or portable (e.g. worn or held by the person being monitored). The CCM 15 may convert the biosensor data stream from an analog signal to a digital signal 21 (depending upon the sensor utilized), perform preliminary signal processing 22, display a limited form of data (i.e. current measured value) and encrypt and encode identification tags 16 to the converted and processed data. The DCU 30 can receive preliminarily processed data 36, perform necessary additional signal processing 34, compilation of subsequently transmitted data sets 32 from the CCM 15 and store data 38 as necessary. The DCU 30 may periodically transmit 36 the data to a remote database management system 50 for further signal processing 52 (decryption, identification), analysis 52, summarization 58, storage 56 and/or action 59. The database management system 50 may also, in response to the summarization of data received, feedback either to the DCU 62, CCM 64 or both.

Figure 3:
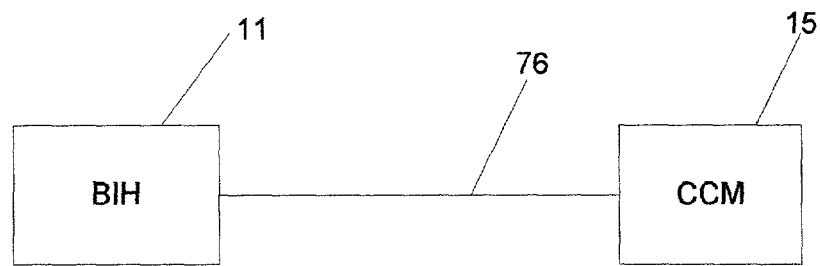
FIG. 3. Illustration wherein a direct communication linkage is established between the CCM and BIH.

In a preferred embodiment (FIG. 3), communication of the BIH 11 and CCM 15 is through a direct physical link 76 to the BIH 11. Examples of the means by which the CCM 15 can be connected to the BIH 11 are: conductive wire, optical fiber, tape or nylon filaments, silicon microvia channels or other methods that physically link the BIH to the CCM.

Figure 4:
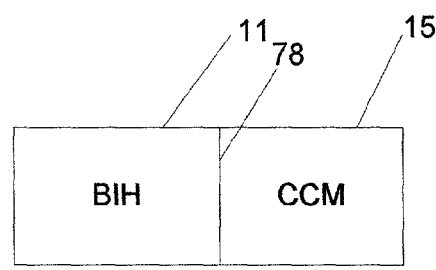
FIG. 4. Illustration wherein the BIH and CCM are integrated into one component.

Alternatively (FIG. 4), the BIH 11 is linked 78 to the CCM 15 fabricated assembly such that no clear delineation is visible between the two components. In this embodiment, both components may reside on the surface of the body.

Figure 5:
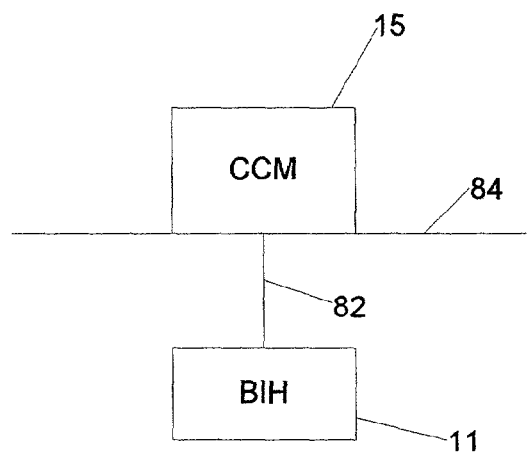
FIG. 5. Illustration wherein a direct communication linkage is established between the CCM and an implanted BIH.

In a second variation of this embodiment (FIG. 5), the CCM 15 is physically linked 82 to the BIH 11, however, in this variation, the BIH 11 is located below (or within) the body surface 84 whereas the CCM 15 resides on the outside surface of the body. The location of the implanted BIH may be sub-dermal, or located within deeper tissues or layers or within organs of the body.

Figure 6B:
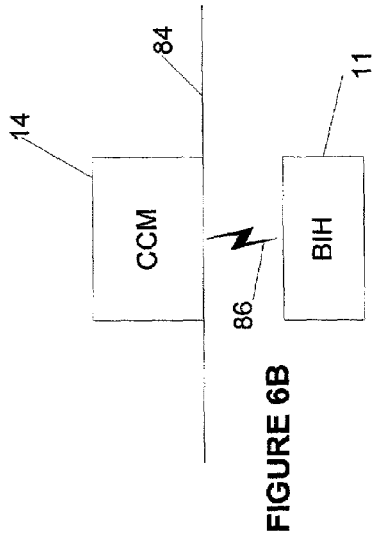
FIG. 6. Illustration wherein an indirect communication linkage between the CCM and a surface-mounted BIH (FIG. 6A) or an implanted BIH (FIG. 6B) is established.
Figure 6A:
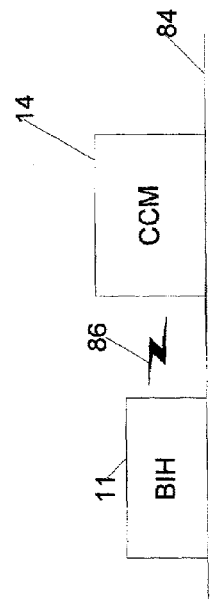

In yet another variation of this embodiment (FIG. 6), the CCM 15 is not physically linked to the BIH 11. The CCM 15 resides on the outside surface of the body 84. The BIH 11 is located either on the outside surface of the body (but not physically linked; FIG. 6A), or is implanted below the surface (but not physically linked; FIG. 6B). The CCM 15 and BIH 11 communicate through a wireless means 86, such as electrical, optical or acoustic transmission. The location and manner of the mounting of the CCM and BIH on the host body are determined by the application or bioparameters to be measured.

More than one CCM/BIH assemblies may be employed for measurement of physiological bio-parameters. Bio-parameters of the mammalian subject are obtained by a plurality of BIH assemblies and collected with intra-device communication, signal monitoring and analysis, e.g. signal/time differential sensing of electrical impedance between multiple assemblies. Variations of this approach would be the inclusion of multiple multifunctional CCM/BIH assemblies for data collection and transmittal.

Figure 7:
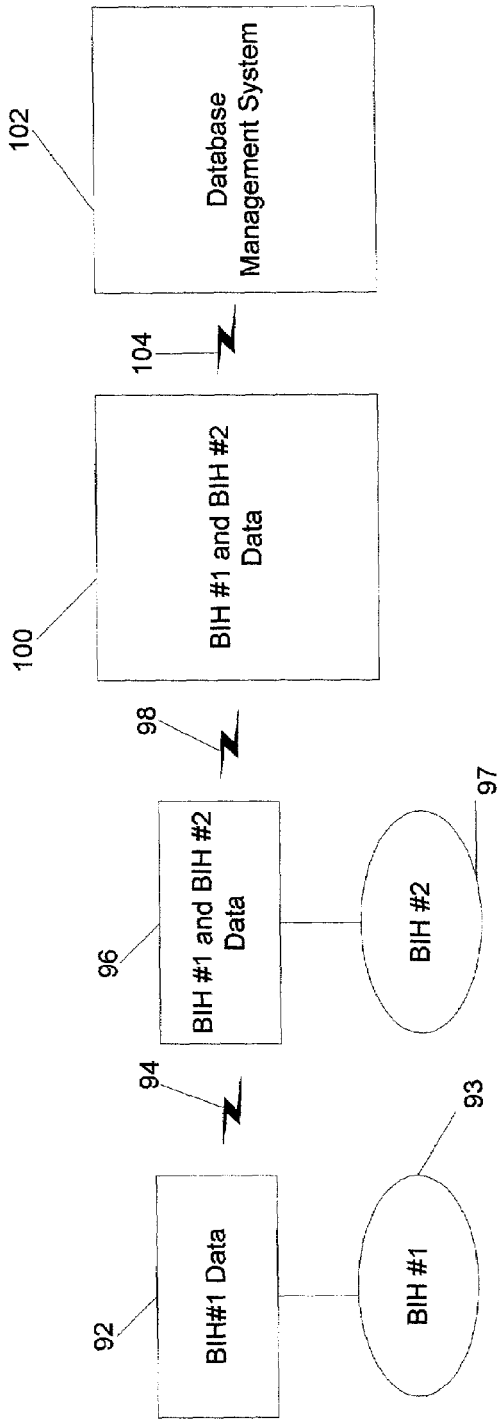
FIG. 7. Block diagram illustrating the use of more than one CCM to relay data from the BIH.

One feature of the present invention is that multiple CCMs may be employed to provide a more robust communication of data to databases if a DCU or mammalian subject is out of coverage range or experiences some type of data transmission interruption or interference (FIG. 7). For example, a CCM #1 92 located on a subject transmits 94 the collected data from BIH #1 93 and processed bioparameters to a CCM #2 96 located on an adjacent mammalian subject. CCM #2 96 would then transmit 98 data received from CCM #1 92 and its own collected bioparameter data from BIH #2 97 to an available DCU 100, which would then upload 104 both data sets to a remote database management system 102. The transmitted data from both CCM #1 92 and CCM #2 96 will be encrypted and encoded to ensure that the information is secured and transmitted to authorized communication devices only. This example may be extended to include two or more CCMs to relay the data to a DCU.

Figure 8:
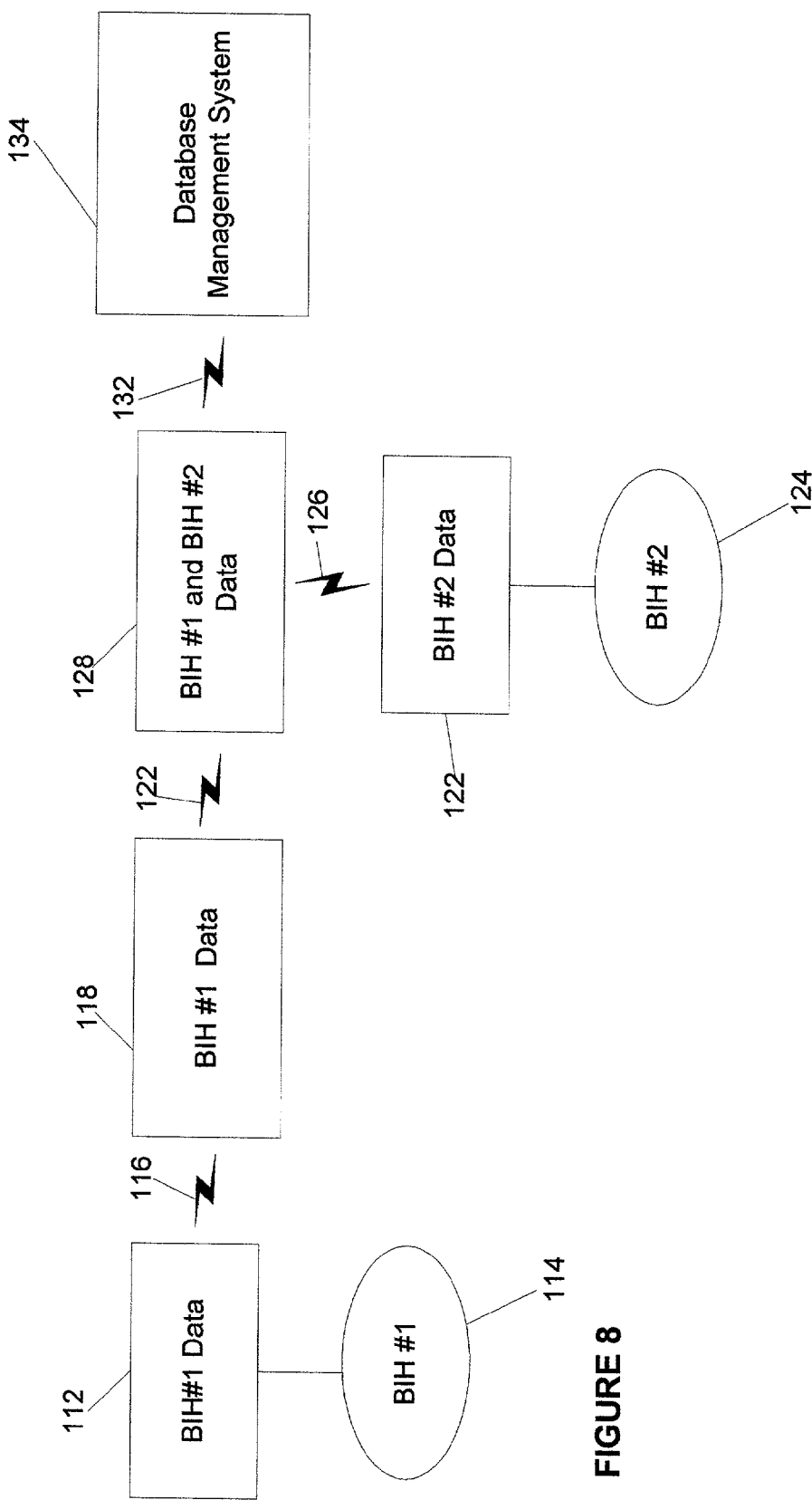
FIG. 8. Block diagram illustrating the use of more than one DCU to relay data from the BIH.

Improved communication between devices may also be accomplished by an alternative embodiment (FIG. 8), where multiple DCU's 118 and 128 are used to relay the bioparameter data to a remote database management system 134 if the mammalian subject is out of coverage range or experiences some type of data transmission interruption or interference. In this example, a CCM #1 112 receives bioparameter data from BIH #1 114. CCM #1 112 transmits 116 the bioparameter data to DCU #1 118, which in turn transmits 122 the signal to DCU #2 128. DCU #2 128, which also receives 126 data from BIH #2 124 through CCM #2 122, transmits bioparameter data from both BIH #1 114 and BIH #2 124 to a database management system 134.

Improved communication may also be achieved with the use of multiple CCMs receiving appropriately coded signals or data from a transmission source other than a DCU. Such a signal may take the form of a radio transmission sent by common carrier transmitters, e.g. commercial radio stations, which may provide an alternative means to communicate to CCM assemblies. Such a communication means may prove useful for reaching one or more measured subjects such as the need during natural disasters or civil emergencies to ensure proper functioning of BIH/CCM assemblies.

BioInterface Head (BIH)

The Bio Interface Head assembly picks up one or more external or internal measured parameters, which may include physiological parameters, biomolecules or foreign agents, and transforms them into an easily processable signal, usually electrical or optical. The BIH is comprised of several components. These may include, but are not limited to, sensors, interface or sensor mounting features, data communication features, and structures for limiting movement or ensuring placement on the measured subject of the sensors. A preferred embodiment of the invention includes within the BIH at least one sensor which measures physiological parameters, e.g. temperature or pressure. Surface temperature sensors which can be placed on the thorax, armpit, extremities or other parts of the body surface (Exacon, Inc., D-SFL-1 multipurpose temperature sensor, Wuntronic glass probe NTC Thermistors Series SP or other commercially available thermistor) can be mounted onto the BIH head for temperature measurements. Other sensors may also be included which measure EKG, ECG, pH, biochemicals, biomolecules, gases such as $CO_2$, and other chemical parameters, enzyme-based parameters, radiation, magnetic and physical parameters, such as blood flow, blood pressure or other physical parameters), or other information (e.g. body positioning, GPS location).

The measured data signal from the sensors may be conditioned at the BIH assembly to enhance the transmission to the CCM. Examples for such conditioning are amplification, filtering or encoding. The signal is then transmitted to the CCM. In cases where the BIH is integrated into the CCM, the connection may be very short. The connection may consist of an on-chip connection, which would minimize the distance between the CCM and BIH.

Depending upon the application, the BIH may comprise a contiguous unit with the CCM whereas in other embodiments, the BIH may be a separate unit from the CCM, linked by either electrical, optical or other means to convey data between the CCM and the BIH. The BIH may be a replaceable unit connected by physical or wireless means to the CCM. This feature permits the ability to replace the BIH with either a new, different or replacement BIH assembly while maintaining the same CCM. In addition, one design feature desirable in certain applications is that if the CCM or BIH is abruptly moved or otherwise displaced, it disconnects from the BIH such that the sensor system, including those forms transdermal in aspect, remain intact and non-moved.

The BIH, in addition, may also contain replaceable, disposable sensors mounted within or otherwise attached to the BIH mounting unit. This feature permits the ability to replace sensors within the BIH with either new, different or replacement sensor units while maintaining the same CCM-BIH assembly.

The BIH may utilize surface or non-invasive sensors for obtaining bioparameter data, such as temperature or pressure. Alternatively, the BIH may employ or mount sensors designed for obtaining subdermal (or further within the body) measurements. The form of the BIH will accordingly differ depending upon the application, which governs the sensor selection.

The BIH may incorporate sensors that measure and/or transmit data either mechanically, electrically, photonically or by other means. Addition of circuitry or other technology, e.g. photomultipliers, may be added based upon signal-to-noise analysis with each type of sensor.

In addition, the use of photonic systems, e.g. vertical cavity semiconductor laser (VCSL)—derived excitation, coupled to photodetector pickup utilizing optics, e.g. fiber optics, or waveguides, for signal transmittal from the sensor head may be used to communicate between the CCM and BIH. Again, dependent upon signal strength, it may be necessary to locate some of the signal processing functions on the BIH. A photonic coupled system may be less noisy than a corresponding electrical platform, making photonic signaling between the BIH and CCM more desirable in specific situations.

Compatibility of the BIH to the environment (e.g. biofluids) for extended periods will also factor into the design of the sensor platform. Depending upon the environmental conditions, coatings (e.g. silicone, epoxy, synthetic polymers or other materials) or other approaches may be incorporated onto the sensor platform to extend BIH and/or CCM lifetime or to enhance biocompatibility.

Figure 9:
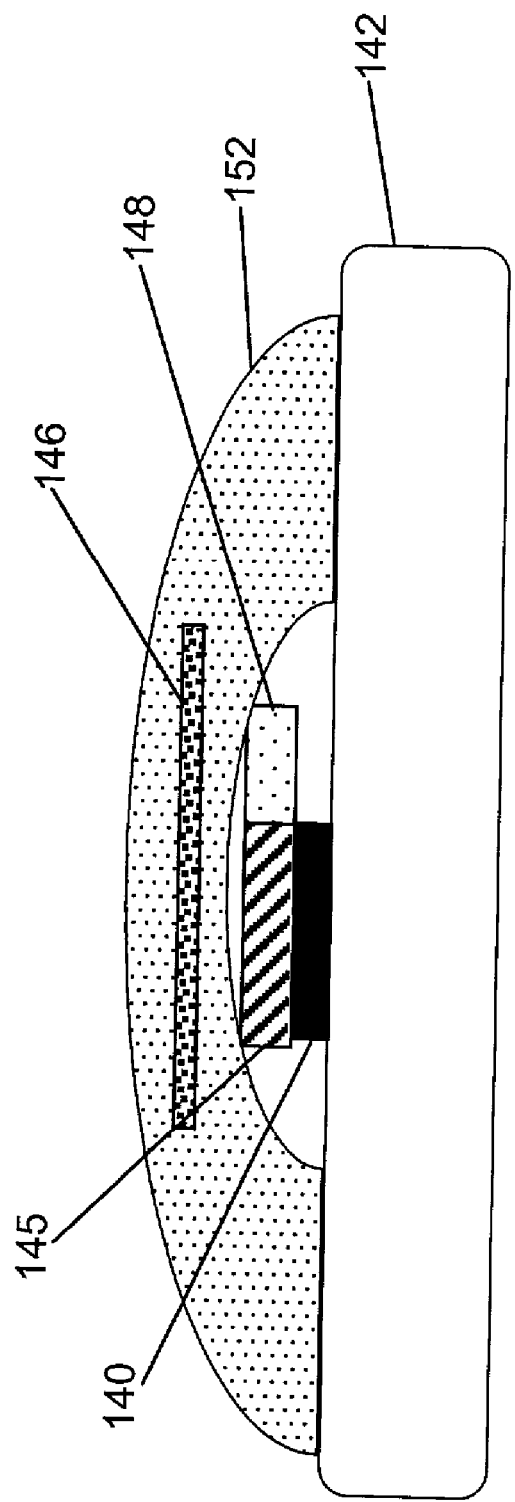
FIG. 9. Partial cross-sectional view of surface-mounted BIH and CCM assembly FIG. 10. Partial cross-sectional view of Invasive BIH and CCM assembly (FIG. 10A) and sensor head assembly (FIG. 10B).

A surface mounted BIH, as illustrated in FIG. 9, is a platform capable of measuring bioparameters from the measured subject with sensors. In simple situations, the sensors 140 are in contact with the uppermost dermal or surface layer 142. An example of this can be found for surface temperature sensors placed on the thorax, armpit, extremities or other parts of the body surface (Exacon, Inc., D-SFL-1 multipurpose temperature sensor, Wuntronic glass probe NTC Thermistors Series SP or other commercially available thermistor). In other situations, microsensors, such as microneedles utilized for conducting heat to temperature sensors, may be extended in a transitory fashion from the surface mounted head in order to obtain readings.

The unit itself may be packaged along with the CCM 145 as shown, or may be separated from the CCM but linked to the CCM via conductive wire, optical fiber or other data transmission methods. Sensor systems, mounted within the BIH, may deliver electrical, optical or other type of data signal to the CCM depending upon the sensor type utilized. The unit will also include a transmission and receiving device 146, as well as a power source 148.

Mounting the BIH onto the surface may be done by adhesive patch 152 or by other methods which attach the assembly to the surface or any defined location on the body, e.g. on the skin, tooth surfaces, oral cavity or within other body cavities.

An invasive BIH (FIG. 10) is designed to serve as a platform for biosensors monitoring bioparameters internally or below the surface of the body. It is also designed to link the data to and from these sensors to the surface mounted CCM. One feature to the invasive BIH is its function of linking subdermal (or deeper) sensors to the CCM while minimizing infection and rejection by the host. As such, it may contain several aspects to a design.

An invasive BIH may typically have three main tasks. The first task is to serve as a path or avenue to allow the sensors access to the internal environment, including internal biofluids (e.g. blood, lymphatic fluids, ductual fluids, or any other fluids produced by the body). This environment may be subdermal or located deeper within the body, e.g. the peritoneal cavity, intramuscular, or organs. The second is to anchor or locate a signal transmission device and the third is to hold a sensor or mount for a replaceable, insertable sensor assembly.

These features or tasks are illustrated in FIG. 10. There may be other designs and structures which perform these tasks that are also possible, and this embodiment is not intended to limit the scope of this invention. This design has four main components. The first of this is the external mounting ring 162. This feature is to be made of an inert, hypoallergenic material, e.g. stainless steel, nylon or any other material which does not cause an allergic reaction in the body. Mounting points may be contained on this ring for the external portion of the replaceable, insertable sensor assembly. Anchoring this ring to the dermal layer 164 may be done by utilizing both adhesives 166 and the physical compression of the tissue surrounding the transdermal portion, or any other method which will anchor the ring to the dermal layer. The adhesives employed may be both conventional biocompatible synthetic adhesives as well as materials utilizing the bodies' own ability to form fibrous, contained structures contiguous to the dermal layer (the equivalent of a common scab). This latter point may be accomplished by coating the lower aspect of the mounting ring with appropriate growth factors, adherence molecules and attractants, such as prothrombin activator, vitamin K, thrombin, fibrin, keratinocyte growth factor, activin, proteoglycans, cytokines, chemokines, TGF-beta, TNF-alpha, VEGF, PDGF, FGF, PAF, NGF, IL-4, IL-8, Insulin-like growth factor, integrins, laminin, fibronectin and other factors which promote the cutaneous wound-healing mechanism and formation of an epithelial-like structure around the mounting ring.

Extending below the mounting ring is the second component (transdermal conduit 172), which is a structure (e.g. tube or filaments), that serves as the guide for the insertable sensor assembly. The transdermal conduit is a semi-permanent tube or structure that may be inserted by a clinician and is not intended to be routinely removed or replaced by the measured subject or clinician. In most embodiments, this tube is flexible, hypo-immunogenic and possesses one or more hollow cores. A variety of materials have been employed in the health care industry for use as catheters, including silicon polymers, which have the appropriate ductility and biocompatibility. If necessary, the outside wall may be coated with additional polymers to increase biocompatibility and minimize the possibility of rejection, e.g. polyethylene glycol or other related polymeric materials. To provide additional mechanical strength, a laminate interior comprised of nylon or high strength fiber mesh may be added, e.g. KEVLAR (a nylon laminate), which adds strength while maintaining the required flexibility. Flexibility and ductility are elements for comfort and acceptance of this implant technology.

At the end of the transdermal conduit is the third component, the sensor mounting head 182. This mounting head may also facilitate insertion of the implantable BIH assembly. The mounting head will also be composed of rigid biocompatible materials, such as nylon or other materials that would increase the rigidity of the structure. However, in order to minimize fibrous growth in the region of the implant, it may be coated with appropriate adhesion biomolecules and/or growth factors to mimic the surrounding environment and aid in the integration of the device into the surrounding tissue. In addition, anticoagulation aids (e.g. heparin or other pharmaceutical anti-coagulants) may be present to prevent the adhesion of platelets or other clotting/rejection factors onto the sensor head. The integration of the head into the surrounding tissue may be necessary in order to minimize physical disruption of adjacent cells during routine motion on the part of the individual, thereby lessening encapsulation of the device by fibrous tissue as part of the body's rejection mechanism.

Contained within the head is the fourth structure or component, the biofluid access port 184. This feature provides the means for biofluids to pass into the device for analysis while simultaneously avoiding contamination from the outside environment. To accomplish this, a fine mesh, membrane or frit, or any other material which would provide a barrier for the sensor head, may be employed to prevent the transference or transmission of pathogens into the body. Certain micro-structures, e.g. MEMS or MOEMS based structures, formed with microvias, micro-sphincters, microvalves, micro-openings, or composite nanostructures having a porous character, e.g. a mesh, contained within a surrounding silicon chip can provide the necessary exclusion of particles while allowing fluid and small molecule passage for testing. In addition, this component will have the necessary structural features for packaging within the rigid head component. In certain applications, the access port itself is part of the sensing system, e.g. a pressure sensitive device or thermal sensing unit. The biocompatibility issue has been a significant challenge in prior devices. In particular, cellular debris in the vicinity of the access port might lead to the development of a rejection response or render the sensor ineffective. To minimize this risk, flushing of the vicinity in the region of the access port may be necessary to remove cellular debris periodically. Flushing can be performed either manually by the user, or automatically through the use of channels or compartments which release saline or other physiologically compatible solution upon the sensing of occlusion, rejection or other factors which may diminish the intended performance of the device.

One approach to minimize performance degradation of the device is by the addition of biocompatible fluids 196, e.g. blood substitutes, physiological saline, or other physiologically compatible solutions which may contain bacterio-static agents into the interior of the transdermal conduit. These fluids would either back flush occluding material out of the transdermal conduit or, by virtue of the hydrostatic pressure generated by inserting the BIH assembly 194 into the conduit, force the small amount of cellular debris adjacent to the access port into the surrounding extracellular fluid or interstitial space aiding the body's own mechanism to flush the material away. Other approaches include the addition of appropriate adhesion factors (integrins, laminin, fibronectin and other adhesion factors) to augment the integration of the access port to the surrounding cells, coupled with the use of other microdevices, e.g. MEMS or MOEMS, that remain sealed until activated. Upon activation (based upon communication from the outside system through the BIH assembly), vias open up within the micro device, resulting in micropassages into which extracellular fluid may flow. Micron scale "scrapers" within the microdevice may also be employed in conjunction with flushing to remove debris and gain access to interstitial fluid. Additional approaches, e.g. the use of electrical, or photonic forces, or chemical agents, may also be employed to sweep the charged biomolecules forming the cellular debris away from the access port and/or improve access port function. All of these approaches may be synergistically applied to provide access to biofluids for monitoring. A valved structure may also be utilized to control the quantities and sterility of the biocompatible fluids 196 used to flush the transdermal conduit. This valved structure may be created by insertion of the replaceable BIH assembly 194 into a valve means, which would aid in controlling the added biocompatible fluids 196 as well as regulate backpressure from infiltrating biofluids into the biosensor head 182 and the transdermal conduit 172.

To aid with the manufacture, storage, in-field calibration and insertion of the BIH, a biocompatible hydrogel or similar substance may be used to coat or encapsulate the BIH assembly 194. The conduit 172 and head 182 may also be filled with this hydrogel. The hydrogel may contain preservatives, anti-inflammatory agents, anticoagulants, bioactive agents, e.g. growth factors, cytokines or other bioactive agents, and antibiotics or antimicrobial agents. A form of hydrogel (e.g. select agarose gels, carrageenan gels, collagen gels, or other biocompatible synthetic or natural gels) may also be employed which exhibits the property of either being gel or liquid in nature in a temperature-dependent fashion. In particular, at or around room temperature the material has high viscosity and is gel-like in nature. When raised to body temperature, the material becomes fluid and is absorbed by the surrounding tissue.

Once the transdermal conduit 172 is inserted through the skin or outer membrane, a BIH platform 194 may be passed down through the center core and positioned at the sensor mounting head. The action of inserting the BIH assembly 194 may be performed by a physician, other trained personnel or the mammalian subject directly to replace or change the BIH as needed or as desired. In inserting the BIH assembly 194 down the transdermal conduit 172, biocompatible fluid 196 containing antibiotics and other agents designed to facilitate biocompatibility, anti-inflammation, system sterility and enhance biomolecule access to the sensor may be introduced. This may be accomplished by having a small reservoir of fluid attached to the BIH assembly 194 and upon application of external force, e.g. manually squeezing the reservoir or any other means of depositing liquid, the fluid is forced down into the transdermal conduit and flushes the conduit, head assembly and access port. Alternatively, the BIH assembly being introduced may have a hollow core through which the fluid may flow, and excess fluid will either pass through the BIH into the surrounding tissue or back up the conduit where, by use of backflow valves, a sterile solution is preserved within the conduit and head assembly. In yet another embodiment, other forms of gels, e.g. Pluronic F-127, which are liquid at room temperature but gel when elevated to body temperature, may be utilized to flush the transdermal conduit 172 and then, upon gelling, provide a barrier to contamination as well as some degree of structural support to the transdermal conduit 172 and sensor mounting head 182. In yet another embodiment, the BIH can be an integral part or mounted permanently within or on the outside aspect of the conduit/head assembly.

In certain applications and embodiments, the mammalian subject's own bioenvironment, e.g. a rejection response to foreign objects or materials, may be employed to remove the implanted BIH. That is, the BIH may be composed in part or entirety in materials having finite lifetimes within the body. At the end of the anticipated lifetime, a biocompatible coating would dissolve or degrade, exposing a non-biocompatible surface underneath. Alternatively, components of the BIH may be comprised of materials, e.g. collagens, that would be absorbed by the body over time. In other variations, agents to facilitate rejection, fibrous tissue growth or other means of isolating the BIH by natural mechanisms, may be added through the transdermal conduit 172 to end the BIH's lifetime within the measured subject.

The BIH sensor head 182 will signal or otherwise indicate the type of sensor employed as well as a unique identifier to the CCM 192. The CCM 192, in turn, may communicate this information back to the DCU such that the data stream is analyzed for the correct physiological parameter and the identity of the individual is linked to this analysis.

1.1.3 Independent Implanted BIH

An independent implanted BIH is similar in concept to the invasive BIH described above with similar concerns about biocompatibility, biofluid sampling, etc. One feature difference is that the independent implanted version does have a wireless means to the CCM. The entire device or package will be inserted, maintained and removed by qualified personnel, e.g. physicians, licensed nurses or technicians.

In order to communicate biosensor data, the independent implanted BIH assembly may include the necessary features from the CCM to enable communications with the DCU or will have a wireless communication link to another CCM assembly (which may be surface mounted). In the former situation, the design of the device will include both features of the implantable transdermal conduit and head assembly, BIH and CCM as an assembly. In the latter case requiring data communication to another CCM assembly located elsewhere, a number of additional features such as power source, data transmission, signal processing, and signal encryption capabilities may be built into the BIH assembly. Possible power sources for the BIH include batteries or responder (RF) technology. Alternatively, the measured subject's own energy, e.g. motion, internal chemistry, including ATP molecules, glucose, or other energy supplying compounds, or osmotic pressure, may supply the energy necessary to power the implanted BIH.

1.1.4 BIH Delivery System

The delivery of various compounds and materials, including, but not limited to: therapeutic agents; molecular scale sensing devices or materials; bioactive substances; enzymes; proteins; gene therapy agents; viral-based bio-agents; and/or micro- or nano-scale devices or materials; may also be accomplished in certain embodiments using the BIH. These materials and/or devices may be delivered for a variety of purposes, including, but not limited to: the relief of detected conditions; for preventative treatments; and as mobile sensors, detectors or other aids to diagnosis, treatment or measurement.

The reagents, materials, compounds or devices to be administered may be stored within reservoirs or other containment methods within the BIH and/or CCM assembly. The materials, compounds, devices, etc., may be stored in either biologically active or inactive states. The storage form may include aerosols; compressed gases; liquid storage, e.g. suspensions, solutions or gels; and/or dry forms of storage, e.g. powder, granules or films.

Upon receipt of appropriate data and instructions, the CCM will direct the release of some portion, e.g. all or a fraction, of the material from storage in the BIH and/or CCM for delivery either to the surface of the measured subject or below the surface. In the latter case, transdermal delivery systems may include microprobes extending into or below the skin or other outer membrane, or utilize the transdermal conduit and access port of the invasive BIH assembly. In other embodiments, the storage area and/or release site may include locations or sites located on features built into the head or outside aspect of the BIH/CCM assembly. The delivery site and mechanism may also utilize microstructures, e.g. MEMS or MOEMS-based systems, integrated into either the BIH or CCM and may have micro-valves, microchannels, ports and switches.

The delivery mechanism may include, but is not limited to: fluid pumping; mechanical insertion; chemical reactions, e.g. production of gases or pressure to aid delivery; or electrical means, e.g. ionophoretic transport. Alternatively, the delivery means may include the removal or dissolving of protective layers from regions of the BIH upon instruction from the CCM, exposing the bioagents, materials or devices underneath. The bioagents, materials, or devices to be delivered may be mixed with additional fluids or reagents, e.g. water, physiological compatible buffers and components, dimethyl sulfoxide or other solvents, to facilitate generation of active materials or the absorption or uptake of the materials, compounds, etc. by the measured subject. Once added, the delivery system may signal the CCM as to the addition of the compounds, materials or devices or the addition may be monitored by sensors detecting either the agents directly or indirectly through bioparameters.

Control and Communication Module (CCM)

The CCM is the assembly which links the BIH and the DCU (Data Collection Unit). Typically, the CCM receives data from one or more BIH assemblies and transmits the data to the DCU for further processing. The CCM is also capable of receiving information or instructions from the DCU, another CCM or other communications device. Components comprising the CCM (Hardware or Software; FIG. 12) may include but are not limited to, the signal receiver from the BIH assembly, e.g. electrical, acoustical or photonic signals, a filter to remove extraneous signal and/or noise, memory buffer, analog to digital (A/D) conversion, error diagnosis and/or correction, signal encryption and identification coding, power supply, power supply control, reception/transmission protocol, internal time reference and a means to convey the digitized data to the DCU, such as electrical e.g. radio transmission (RF), acoustic or optical transmission. Individual components comprising the CCM may vary depending upon the type of sensor used, the type and strength of the signal from the sensors, the transmission environment and the availability of DCU's or other receiving devices for transmitting and receiving data or information.

In use, the CCM may take the form of a multifunctional chip assembly mounted onto an adhesive strip or other adhesive material for ease of attachment onto the measured subject. Alternatively, the CCM might be placed onto a device, a strap or integrated into clothing or apparel. In some circumstances, it may be advantageous to mount the CCM internally, e.g. invasively or within a body cavity, in order to minimize device removal and to facilitate use by increasing compliance.

The CCM may be at least one IC (integrated circuit) assembly which may include the following functionalities on-board, depending upon the application and sensors used: A/D signal conversion, signal filtering, memory (Flash RAM/ROM, EEPROM, or other means to store data), controller (including, but not limited to CPU processing, custom microprocessor, one-time programmable microprocessor (OTP), multi-time programmable microprocessor (MTP), field programmable gate array (FPGA), programmable logic controller (PLC) or other types of controllers that are available depending upon the available technology (nano-controllers, optical relays or electrical arrays)), data binning, data transmission encryption and a unique identification (ID tag) as well as functions that were described previously for the CCM, (such as a power supply and antennae for wireless signal transmission and reception to and from the DCU). These functions may be integrated onto a single chip, comprising silicon, gallium or germanium, depending upon the available technology. It may be incorporated into an adhesive patch or device to be worn by the individual to minimize size or bulkiness and maximize comfort.

Modifications to the CCM assembly for adaptation to the implanted sensor platform include but are not limited to the ability to incorporate a bio-fluid reservoir and snap-off mounting to prevent dislodging the transdermal conduit and BIH if the CCM or patch is violently jarred or displaced. Dependent upon the application, the BIH may also be directly assembled onto the CCM assembly in order to reduce the cost and size of the product and improve signal reception from the BIH.

In operation, the CCM receives at least one signal from the BIH. The CCM may amplify the signal through the use of an automated gain control or other means of amplification (e.g. operation amplifier). An analog to digital (A/D) conversion of the received signal from the BIH may be performed if necessary. Other pre-processing methods, such as filtering or signal averaging, may be employed to improve the signal-to-noise ratio. The method employed depends on the type of sensor or application used. The pre-processing also may include error diagnostics (electrical system diagnostics, impedance and other error diagnostic protocols) to detect a problem in the CCM or BIH assemblies, or application, such as communication and/or sensor problem, e.g. a broken wire or an internal sensor fault. This function assures that no erroneous data is generated due to a sensor fault or communication interruption/failure. An error correction algorithm may also be incorporated to enhance the measured signal quality.

BIH and sensor identification (or ID management) is an attribute of the HG system. In particular, the ID management function ensures increased accuracy in sensor type employed and appropriate data tracking and handling to the measured subject. This also enables the DCU to selectively receive information from CCM's that have been addressed to this DCU. ID management provides information about a particular BIH assembly features such as the sensor type or serial number to the DCU. This information may enhance the data communication reliability and identification of measured subjects in a densely distributed application such as a hospital or assisted living environment.

The pre-processed signal is transmitted from the CCM to the DCU. This transmission may be encrypted using unique encryption algorithms to protect the data and allow security of transmission, especially where multiple CCM, DCU or both are used to relay the information. Furthermore, the transmission protocol may include elements, such as differing frequencies, modulation e.g. frequency hopping spread spectrum (FHSS), direct sequence spread spectrum (DSSS), timing, handshakes e.g. check sums. The transmission may be one-way or two-way, depending upon the need for feedback of processed data or information to the mammalian subject. The CCM may include hardware to enable transmission and receipt of signals from one or more BIH, CCM or DCU assemblies.

The CCM may include a time reference, such as an internal clock, for those applications which require measured data to be correlated based upon a time (relative or absolute) or expiration of time. This is important for many medical applications like ECG or heart rate measurement. In addition it may assist in the analysis of data based upon the frequency of a particular measured event's occurrence or the absolute time when a measured event occurred. It further assures correct communication timing necessary for monitoring of physiological parameters.

A power supply is essential for the operation of the BIH and CCM assemblies. It is preferably integrated into the CCM assembly. It may power the BIH if power requirements exist, e.g. MEMS head assembly or active sensors. Two possible solutions are a battery or a responder circuit that is powered by an electromagnetic field e.g. inductively or capacitively charged.

A power control function may ensure proper function while optimizing the power consumption. It includes a start-up mechanism that controls the power delivery to the circuits in order to initiate the first measurement after a power-down phase, and may also include low power (sleep) settings to extend the device use. The system may include multiple power sources to extend the device use e.g. battery and inductive recharging of battery. The power control function will manage the multi power source configurations.

A feedback device may provide simple user information. This may be for example an light emitting diode (LED), piezo beeper or a mechanical vibrator/clicker that may be used to indicate whether a measurement has been completed successfully or whether an error has occurred. In addition, an alert/feedback mechanism may be employed in those situations where critical threshold parameters, e.g. temperature, are exceeded. This alert/feedback system would use the display (if present) and the feedback device (if present).

The CCM also may in certain circumstances contain a means of displaying the data being transmitted, e.g. a flexible or rigid visible display such as a liquid crystal display (LCD), organic light emitting diode display (OLED), magnetically reactive polymer displays (e.g. electronic ink), passive or active colorimetric or color based alert displays. The display unit may be mounted onto the CCM. Alternatively, the CCM may mount a simple audio alarm or alert.

Data Collection Unit (DCU)

The Data Collection Unit (FIG. 13) may interrogate the CCM and receive a signal from one or more CCM's. The DCU may convert the received signal into a form that can be processed by the DCU control system e.g. a microcontroller. The DCU is intended to have more extensive means for data processing than the CCM. As a result, this may allow more complex signal processing and analysis. This function may improve the analysis of signals received and may enable management of data received from other applications. The results may be transmitted to a remote database management system through a communications network, e.g. a cellular phone network or the Internet. With this method, the data may be remotely collected, analyzed and summarized. The processed data may then be provided to other persons, e.g. a measured subject, clinician (physician), or authorized third parties. The receiving party may also communicate back to the measured subject or other authorized third party using the same communication network. This may enable the measured subject and clinician to remotely communicate diagnostic knowledge and/or actions resulting from review of processed data.

The utility of the device requires that the DCU have several attributes. These include, but are not limited to: the ability to transmit to and to receive data streams from the CCM, to communicate these data to secondary sites of analysis using such means as linkages through internet communication-based systems, cell phone-based communication devices, personal alpha-numeric paging networks or hardwired direct communication systems configured to receive and analyze such data streams. In addition, the DCU may also have a user input device, e.g. a keyboard, touch screen, as well as a display or actuators, e.g. a beeper, to serve as a user interface. A power supply for the DCU may be mobile, e.g. a rechargeable battery or it may be wire-bound, such as might be the case in wall mounted DCU units.

As such, one form of the DCU may be an accessory module placed within or otherwise connected to preexisting communication devices such as hand held cellular telephones and PDAs.

As the signal transmitted to the DCU may be weak, the DCU might be directly connected by wire or other means directly to the CCM. Alternatively, the DCU might be physically separate from the CCM and receive the signal by such means, but not limited to, electrical, photonic or mechanical (e.g. acoustical) generated signals. The HG system as a whole collects more data and measurements over time, which improves the diagnostic knowledge on the mammalian subject.

The remote database management system will store, analyze and summarized the collected data in a real-time environment. Custom algorithms and neural analysis will be used to interpret the collected data, with measured subject or clinician controlled customizable variables. This analysis will be summarized and either made available to the measured subject and/or clinician automatically by either posting the data in a system which would display e.g. Web based portal, or transmit the summarized data to the clinician and/or measured subject, this transmission may be a through a wireless communication system, a land based system e.g. phone call or facsimile, or printed and delivered to the physical location e.g. U.S. Mail, or other mail delivery system.

The data may be transferred from the DCU into a data management system which may further analyze the collected and transmitted signals/data. One of the advantages of the HG system with its continual monitoring allows the establishment of individual baseline measured bioparameters as well as inclusion in and comparison to a larger bioinformatics database. This may facilitate identification of individual deviations or anomalies, as well as discerning population trends. This contrasts with current methods having transient or periodic measurements taken of an individual, e.g. once a day/week, which are less likely to detect deviations or anomalies.

Data Transceiving

For both the connections between BIH and CCM as well as between CCM and DCU, transmission protocols define how the data is transmitted (FIGS. 11–13). They assure compatibility of different BIH, CCM and DCU models and high system reliability. The transmission protocols may vary in complexity depending on the application. For example, a preferred embodiment in the case of a wire-bonded BIH-CCM link, would be a transmission protocol as an analog resistance signal that is read in defined intervals. If a wireless transmission is used, the transmission protocols will be much more complex. Another factor that has an influence on the transmission protocols is whether the transmission is unidirectional or bidirectional. Bidirectional transmissions allow certain features like electronic handshaking, but require more hardware and energy resources.

A protocol definition includes the physical characteristics of the data connection (e.g. RF or infrared radiation, frequency, modulation types). Further, the data transfer mechanism may be specified. This may include synchronization and handshake mechanisms as well as repetition rates. The data structures of the protocol may define the amount of data that can be transferred. Typically the data is organized in blocks or packets that are sent repeatedly at specified intervals. As an example, a protocol may define a transmission block consisting of synchronization bits, an address field that contains ID information, a data field containing the data generated by the CCM from the BIH input and a checksum field allowing testing for data integrity at the receiver's end. The length of the data block variable may vary. This will be useful in minimizing power consumption and maximizing device lifetime.

For two-way transmissions, an electronic handshake is possible where the receiver indicates the successful reception of data. If the handshake signal indicates that the data was not received correctly the sender unit may retransmit. If there is only one-way transmission of the signal, it may be helpful to transmit the data signal more than one time in order to increase the likelihood of signal reception.

If a system is designed to have multiple devices sending data to one or more receivers using one-way transmission, it may be advantageous to use different repetition frequencies for the sending devices. Thus it may become more likely that sending devices do not interfere with each other. This problem may not occur with two-way transmissions since the sending device transmits by request only.

Either custom or available protocols (e.g. GSM, Bluetooth or IP) may be used depending upon the application, devices, environmental conditions (e.g. high noise or signal interference) and transmission requirements.

Based upon the above considerations and those in previous sections, a preferred embodiment for wireless communication between the CCM and DCU would be by RF using a frequency hopping spread-spectrum signal employing wireless medical band frequencies, e.g. between 609 to 613 or 1390 to 1395 MHz. The means to communicate would be two-way, employing electronic handshaking between the sender and receiver. The communication protocol would consist of information packets comprised of four sections: a header section; an 64 bit address section (therefore having $2^{64}$ possible numeric combinations for the device identification); an encrypted data section (encrypted using an algorithm based upon the address section ID); and a checksum or error correction section.

A preferred embodiment for wireless communication between a BIH assembly and a CCM assembly would be similar to the above preferred embodiment describing communication between a CCM and DCU unit. Conversely, data exchange between a DCU and higher level systems would employ existing communication protocols especially with regards to data encryption. In this case, a preferred means of encryption would be existing 128 bit TCP/IP based encryption at the SSL layer of signal transmission.

EXAMPLES

Uses and Applications of the HG include uses involving the measurement of physiological parameters, including but not limited to, temperature, blood pressure, heart rate, respiration, electrical measurements (e.g. EKG or ECG), pH, $CO_2$, $pO_2$, biochemical substrates (e.g. glucose oxidase, phosphatase, vitamins, nutraceuticals, hormone levels, etc.), radiation and magnetic spin states. The parameters may be useful indicators of physiological events, such as ovulation, or indicate abnormal physiological events, such as microbial infection, heart attack or diabetic shock.

Although the examples below are indicative of the type of uses the HG system can be applied to, they are not meant to limit the scope of the invention. Those of ordinary skill in the art can appreciate the many applications that the HG system could be used in, and with no undue experimentation, different sensors can be used to adapt to the application needed for each occasion.

Use of the HG to Monitor Temperature Changes in Patients

Figure 14:
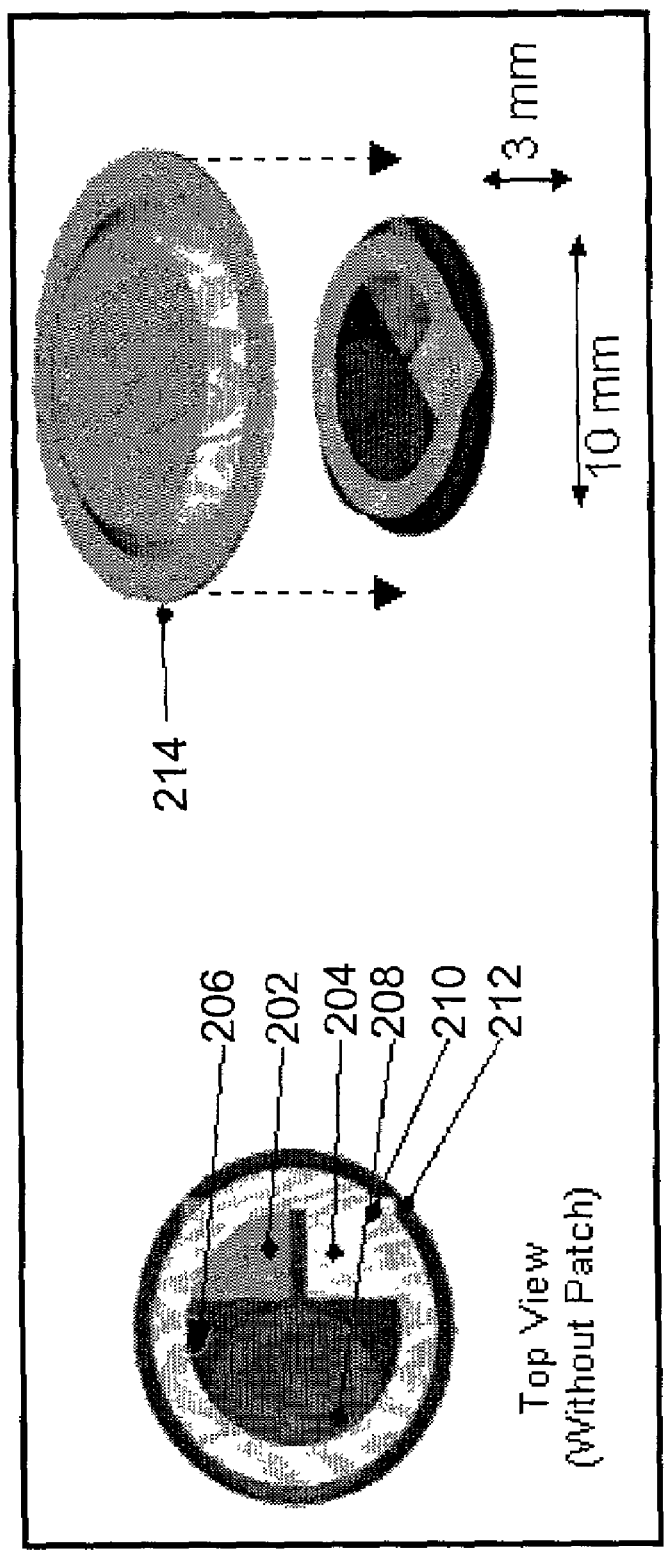
FIG. 14. Views of a surface mounted BIH/CCM assembly

FIG. 14 depicts a HG configured to measure temperature changes either at the surface of the epidermal layer or subsurface in the dermal layer. For temperature measurements at the surface, the CCM 204 and BIH 202 are integrated into one single unit, where the BIH is in direct communication with the CCM. A power source 208 and transmitter 210 are included, where all components are mounted on a suitable substrate 212, and attached to the mammalian subject using an adhesive patch 214. The BIH contains sensors 206 that measure temperature changes, and can consist of one of many types of temperature sensors. A preferred embodiment of surface temperature sensors are thermistors, which are miniaturized, semiconductor-based devices capable of high sensitivity and resistance to extreme environmental conditions. Thermistors are readily commercially available (e.g. Precision Engineering, RTI Electronics, Inc., Wuntronic, Inc. and other manufacturers of NTC and PTC Thermistors), and can be custom fitted to many different applications. Temperature sensors can be placed on outer body surfaces, including the thorax, armpit, extremities and other body surfaces, as well as within cavities, such as the nasopharynx airway, oral cavity and in the ear canal in close proximity to the tympanic membrane (Exacon, Inc., D-TM1 sensor). Other examples of suitable temperature sensors include metallic wire (such as platinum) resistive temperature sensors, thermocouples, semi-conductor p/n junctions as well as other silicon-based diode temperature sensors and band-gap based sensors. Temperature sensitive materials, such as liquid crystals, may also be utilized which have a detectable change in physical properties that is proportional to a change in temperature. Alternatively, temperature sensors may consist of microneedles or other materials penetrating the dermis to more accurately measure the measured subject's temperature (Exacon, Inc. DN1205 and DF1350A). The temperature in this case would be measured by either thermistors or other gauges within the needles, etc. or by conducting the internal temperature back to the surface by heat conductive materials, e.g. conductive metals or organic materials with high heat transference. Changes in the temperature sensor 206 are automatically communicated to the CCM 204, which automatically relays the data stream to a remote DCU unit located either on the person, or to a collection station nearby.

An example of the utility of a temperature sensor incorporated into a continuously monitoring HG system is seen for monitoring of an ovulation event. Detectable physiological changes, such as temperature, occur when the egg is released from the ovary into the fimbrae of the fallopian tubes and eventually into the uterus. Fertilization of the ovulated egg must occur within a narrow window (24 hours) of the ovulation event, making timing of sexual intercourse essential for a successful fertilization event. Although detectable, the temperature changes are minute relative to basal body temperature. Therefore, establishment of an accurate baseline temperature is critical for successful prediction of ovulation. Since basal body temperature is circadian in nature, this requires repeated temperature monitoring throughout the day in order to get accurate baseline values. The HG will continuously collect data and establish accurate baseline values for a given time period. A rise in temperature as compared to the baseline values indicates onset of ovulation. Upon that detected rise, the data collection unit will alert the patient through various communication systems, including but not limited to a remote paging system, telecommunications pathway, e-mail or other internet linkage, voice-mail linkage, through the patient's care provider or other types of communications pathways.

In order to obtain repeatable core temperature readings, it is important to select an appropriate site for placing the sensor system. One such location would be an intrauterine or vaginal placement of the device. In this situation, the BIH/CCM assembly may be packaged in the form a biocompatible capsule or other non-irritating shape and would adhere to the surface either through mechanical, e.g. adhesives, microfilaments or hooks, or be held by physical placement, e.g. as a part of a larger loop or inserted device. In such a form, the BIH may mount additional sensors beyond those of temperature, including sensors to detect cyclic hormones, e.g. luteinizing hormone, follicle stimulating hormone, progesterone, estrogen, or their metabolites, or other biomolecules passed into the reproductive tract that would serve as indicators of follicular status.

In general, monitoring temperature changes is important for other physiological conditions, including the early indication of short term infectious states (general increase in temperature) a sign of shock (general decrease in temperature), non-compliance with therapeutic regime causing localized temperature shift (diabetes, hypertension), or long term deviations or shifts in temperature which are indicators of illness (arterial sclerosis) that are not easily detected with current diagnostic methods. In addition, monitoring temperature is routine in studies or situations where monitoring of patient vital signs is necessary, such as in premature infants, infants, daycare children, geriatric patients or hospital situations.

Veterinary Applications of the HG for Monitoring Temperature Changes

Monitoring temperature changes is not only important for humans, but also in the veterinary field. An increased temperature is a general indicator of infection, and may be an important early indicator to stop the spread of an infectious disease. One such agent responsible for decreased production of milk in dairy cattle is *Pasturella hemolytica*. The information from a device that can detect changes in temperature can be relayed to a data collection unit. The data is analyzed, allowing a farmer to identify the individual through a unique ID assigned to the BIH/CCM device attached to the animal, and isolate the contagious animal before it spreads through the herd. Depending on the size of the animal, the device need not be miniaturized, circumventing the need for extensive engineering. The device could also monitor other bioparameters, e.g. including those relating to general health, reproductive status, nutritional status or activity.

Other veterinary applications include the use of the device in monitoring laboratory animals during experimental manipulations in order to simplify the measurement of important physiological parameters, which indicate the efficacy or non-efficacy of pharmaceutical or other types of treatments. For example, laboratory rats may be equipped with a BIH/CCM assembly and monitored in a continuous or periodic fashion for vital signs, such as temperature, respiration, heart rate and other physiological parameters. BIH/CCM assemblies from several laboratory rats may be transmitted to one DCU. The amount of BIH/CCM assemblies transmitting to one DCU may be limitless because of the encryption and data identification transmission, as well as handshaking, protocols which will be employed. The DCU may then transmit data from the plurality of BIH/CCM assemblies to a remote database management system for further analysis and summarization of the data. This may potentially streamline the data gathering process, allowing more experiments to be conducted in a shorter period of time with no animal handling necessary.

Use of the HG to Monitor Physiological Parameters at the Surface of the Skin

Additional physiological parameters could be measured using the above technology at the surface by replacing the temperature sensor device with another application appropriate sensor. Examples of this include heart rate (pressure detector, strain gage, optical surface tension, electrical output or other technologies), respiration (pressure detector, optical surface tension, strain gage, electrical output or other technology), electrocardiogram measurement (Ag/AgCl electrodes; other technologies), surface pH (some type of electrode), oxygen consumption (Clark electrode, partial pressure of $O_2$, luminescent quenching) and other physiological parameters. Other surface monitors include sensing chemical and biological elements such as non-invasive glucose monitoring through the skin for diabetic patients.

Use of the HG for Vital Sign Monitoring in Patients

In addition to monitoring a single physiological parameter, multiple sensors could be incorporated onto the same BIH to allow multiple parameters to be measured simultaneously. These multiple parameters may be measured by using one or more BIH assemblys that would contain one or more sensors, appropriate to the application, e.g. pressure sensor to determine HR and micro-cantilever to sense potassium discharge through the skin, measuring and communicating the collected values to the CCM, which would filter and combine the data and transmit to the DCU. The DCU would then complete the signal processing and interpret (calculate) the signals into the appropriate application specific format e.g. Heart Rate, or use this data to then project or estimate a health parameter that is highly correlated to the measured value, e.g. daily calorie consumption. This would enable the continuous monitoring of the measured subjects vital signs, e.g. heart rate, respiration rate, potassium discharge in both a hospital setting, as well as in ambulatory use. An example of a use of the HG in vital sign monitoring is found for infants that may be predisposed to Sudden Infant Death Syndrome (SIDS) premature infants could be fitted with one or more BIH/CCM assemblies which would include sensors that monitor blood pressure, respiration, oxygen consumption, heart rate, ECG and temperature. The unit is miniaturized to decrease risk of removal or rejection by patient, as well as to decrease the surface area variability that may pose a problem for smaller patients. In addition, the unit is thermally insulated to decrease the effects of volatile ambient environmental temperatures, such as those found in an incubator, may have on patient temperature. The sensors on the BIH can either be in direct communication with the CCM, or can communicate with the CCM wirelessly, such as through radio frequency or other means of telemetry. Wireless connection of the CCM with the BIH may prove advantageous for sensors that require multiple locations to accurately determine physiological value. The CCM transmits the data stream generated by the multiple sensors on the BIH to the DCU. The DCU can collect sufficient data points to generate reliable current values, and also monitor the patients condition such that upon triggering a pre-determined value, the uploading of information by the DCU into the remote data analysis system enables the clinician to be alerted if a measured parameter moves outside a preset range. This clinician alert can be provided through existing telecommunication systems or with the wireless data communication system with in the HG.

An alternative use of the multiple sensors system would be to monitor multiple parameters that when combined are statistically correlated to either an illness or health maintenance factor. One such embodiment is the use of temperature, heart rate, respiration rate and potassium discharge through the dermis in order to obtain an assessment of kilo-calorie expenditure. This is envisioned as a method to better manage overall health with a measurement of energy expenditure to that diet and weight may be more precisely coordinated. Temperature sensors include thermistors, metallic wire (such as platinum) resistive temperature sensors, thermocouples, semi-conductor p/n junctions as well as other silicon-based diode temperature sensors and band-gap based sensors. Respiration rate may be monitored by chest cavity distension and employ sensors such as strain gauges, including those based on Wheatstone Bridge resistance change measurements, pressure transducers or bands worn around the chest coupled with strain gauges to evaluate chest expansion. Suitable ion specific microelectrodes or related sensor devices may measure potassium discharge. When combined, a profile of these measurements indicate energy consumption and coupled with other patient specific parameters such as weight, would describe kilo-calorie consumption.

Use of the HG for non-invasive Blood Pressure Monitoring in Patients

In addition to monitoring a multiple parameters on a single BIH, various types of physiological parameters may be determined indirectly (correlated) or calculated from values obtained from a plurality of non-invasive or invasive BIH/CCM assemblies located on the measured subject, and using preset variables such as distance, time or location in the calculation/correlation of the parameter.

An example of a multiple non-invasive BIH/CCM application would be the calculation of blood pressure. The blood pressure would be calculated by the DCU using measurement data acquired from two or more BIH/CCM assemblies with one or more of the sensors previously noted to measure the physiological parameter (i.e. heart rate can be measured with a pressure transducer sensor). This non-invasive system is of particular value to clinicians and patients today because of a prevalent condition called the "White Coat" effect. This condition is experienced by many patients today due to anxiety associated with being at their clinician's facility, causing their heart rate and blood pressure to be elevated while in the clinician's facility. As a result, many patients are either misdiagnosed with hypertension or required to return to the care providers facility numerous times to validate the clinicians diagnosis. By enabling clinicians to remotely, automatically and continuously monitor the patients blood pressure they would be enabled to better diagnosis the presence of hypertension and accordingly take the necessary diagnostic actions.

Blood pressure can be calculated in the DCU by locating two BIH/CCM assemblies on the measured subject at a set distance or location. By locating at least two devices on the measure subject, separated at a specified distance, then measuring the heart rate (diastole) from both BIH/CCM devices, then transmitting this data and a time reference for each of the measured values to the DCU. Then inputting into the DCU other relevant variables of the measured subject the Blood Pressure could be calculated. Those inputted values could include the measured subjects gender, weight, height, age, and ethnicity.

In addition to providing the blood pressure values this application would also enable clinicians and patients to monitor patients compliance to therapies prescribed or recommended by the clinician. By enabling either direct measurement or calculation of parameters in a remote continuous environment changes in behavior and/or compliance can be detected. Hypertension is typically treated with a therapeutic medication that must be taken by the patient at clinician prescribed intervals e.g. every 8 hours, if the patient does not take the medication the illness may reappear i.e. blood pressure rises. This application of he technology would enable the detection of non-compliance and reminder to take their medication. The feature of the HG as a compliance monitor is applicable to most of the applications envisaged including both the non-invasive and invasive applications.

Use of the HG to Monitor Blood Parameters in Patients

A HG may be configured to measure various physiological parameters of blood. An invasive BIH assembly is implanted into the patient consisting of sensors that monitor oxygen levels, carbon dioxide, pressure, pH and other physiological parameters important in assessing patient health and condition. The BIH assembly may itself consist of a needle, designed to self-insert into a vascularized compartment, such as a blood vessel. The BIH assembly may also be inserted into the patient with the aid of a surgical instrument that makes a small incision and guides the BIH assembly into the patient, such as a trocar or other surgical instrument. In addition, surgical implantation techniques will be used for implants that are deeply embedded (i.e. below the hypodermis/subcutaneous layer) into the patient host. It is essential that all implantable devices be sterilized prior to insertion into the patient.

The BIH assembly may comprise a flushing system, designed to decrease trauma and adherence of the BIH assembly onto surrounding tissue. This biofluidics system would contain physiological solutions, such as saline, and may also contain antibiotics, antifungal, antimicrobials, or other compounds designed to inhibit the growth of infection-causing organisms. The biofluidics system may also contain anti-inflammatory agents as well as other agents to locally suppress the immune system surrounding the BIH assembly to decrease rejection incidence and increase the longevity of the sensor unit.

After insertion of the BIH assembly, the assembly is adhered onto the skin with specialized adhesive biocompatible materials (transdermal patch) that allow ventilation of the transdermal conduit while maintaining sterility of the assembly. The transdermal patch may be comprised of microporous nylon, thermoplastic microfibers, polypropylene, other polymers or other microporous films which form a barrier against extrinsic liquids, yet enable water vapors, i.e. perspiration and other bodily fluids, to flow freely through the fabric. The fabric should also insulate external conditions from influencing the function of the sensors, such as temperature, pressure, partial $O_2$ pressure and other physiological parameters affected by extreme environmental conditions. The BIH assembly may communicate directly with the CCM assembly through nylon tape, filaments or metal wire connections, or communicate wirelessly via RF or any other telemetry technology, continuously transmitting data from the BIH sensors to the DCU. In order to decrease the risk of occlusion of the sensors or accretion of biological materials onto the sensors that would hamper performance, the biofluidics system may automatically flush the biosampling access point area upon detection of build-up or adherence of material onto the sensor head or at defined time intervals. Alternatively, the region may be flushed either manually or upon replacement of the biosensor component. The detection of biological material build-up may be through sensors which sense changes in pressure or optical clarity of the environment immediately surrounding the sensors or by any other means that can detect accretion of biological materials that would hamper sensing ability. The transdermal conduit incision area may also be manually flushed periodically to decrease adherence of biological materials on the sensor itself.

Data collection and analysis of signal output from the implanted BIH sensors will depend upon the implantation depth of the sensors. Subcutaneous implants could either transmit data to the CCM directly through nylon tape, filaments or insulated metal wire connections, or communicate wirelessly via RF on any other telemetry technology. Implants that are below the subcutaneous layer and into underlying organs may require wireless telemetry for communication of sensor data to either the CCM or DCU. This wireless transmission may be electrical (RF) or acoustic.

Use of the HG to Measure Glucose, Fructosime and Hemoglobin lac levels in Patients The HG may be configured for measuring glucose, fructosime and Hemoglobin lac levels in diabetic patients. Determining accurate levels of these three elements is crucial to achieve metabolic control of diabetic patients in order to avoid hypo or hyperglycemic situations. Specific knowledge of glucose levels allows diabetics to self-regulate exercise, diet and insulin regimens, a condition crucial to avoiding adverse clinical situations.

Traditional methods of monitoring glucose levels includes multiple blood sampling, through finger pricking or other means, and measurement of glucose levels through glucose oxidase/peroxidase colorimetric reaction.

Non-invasive methods of measuring glucose levels have been developed, including the use of reverse iontophoresis to measure glucose levels, the extraction of glucose from interstitial fluid and the use of infrared laser for measuring levels of glucose in fluids. Glucose sensor methods could be incorporated into the BIH assembly of the HG for continuous glucose monitoring. By doing this, more accurate baseline measurements could be obtained with automatic downloading of information from the different sensor systems. Pre-set sensor levels could alert the patient to hypo- or hyperglycemic levels through various telecommunication pathways, including a remote paging system, telecommunications pathway, e-mail or other internet linkage, voice-mail linkage, through the patient's care provider or other type of communications pathway.

More elaborate sensors could also be used which may provide more accurate measurements than currently achieved with non-invasive glucose monitoring systems. An implantable sensor with glucose oxidase at the tip of the BIH sensor would detect glucose through a colorimetric reaction, similar to what is obtained with current hand-held glucose monitors. In addition, other sensor systems, such as electrical detection, potentiometric detection, or any type of detection method could be used in conjunction with the BIH glucose sensing head. For example, deposition of glucose oxidase on self-assembled polypyrrole films would allow measurement of glucose levels through an electron-transfer reaction, allowing levels to be determined according to the relative conductivity of the film (Ram et al, 1999). Self-calibrating structures (microchannels, vesicles, microcompartments) could be incorporated into the silicon wafer microstructures, allowing automatic calibration of the sensor at set intervals throughout the day.

Use of the HG to Measure Drugs or Small Biomolecules

Drugs and other small biomolecules could be monitored using the above technology at the surface by replacing the invasive glucose sensor on the BIH with another appropriate sensor, depending upon the application. (This sensing may be also enabled with an application orally.) Drug monitoring is useful for comparing the efficacy of drug treatment regimens with levels of the compound in vivo in patients. Drug monitoring also overcomes potential polymorphic differences between individuals that could result in over- or underdosing of patients due to differences in drug metabolizing enzyme activities. Drug sensors used would include specific antibody-loaded sensors, enzymes specific in the metabolism of various drug compounds (cytochrome P-450 enzymes, etc.) and other technologies utilized in the detection and measurement of therapeutic pharmaceutical compounds. Sensors could also monitor drug tracers that pharmaceutical manufacturers routinely include in therapeutic formulations. Using tracers to monitor the presence of the prescription drug in the body may assist in determining compliance or effectiveness of therapies, as well as identifying possible counterfeit formulations that may be in use by the patient.

Sensors that monitor the presence of illicit drugs could also be incorporated into a BIH. Sensors important for this application include the monitoring of cocaine, heroin, marijuana, amphetamines and other illicit compounds that would require monitoring on a regular basis. Any detection of illicit compounds in an individual would result in the automatic notification of the appropriate legal authorities. In addition, alcohol levels could be monitored by using pre-set levels determined by the laws of each state. Upon the elevation of alcohol levels beyond these pre-set levels, an alarm would be triggered whereby the appropriate authorities would be automatically notified. For both the detection of illicit compounds and illegal alcohol levels, a feedback loop would also automatically disengage motor vehicle operation, preventing the individual from operating any motor vehicle connected to any of the telecommunication systems listed above.

Use of the HG in Monitoring Serum Proteins and Microorganisms

The HG could also be configured to measure serum protein levels. For example, levels of atherogenic markers, such as high-density lipoprotein, low-density lipoprotein or lipoprotein-a may be measured with antibodies attached to the sensor head. The antibodies may be attached to microcantilever structures and detected through optical or potentiometric methods, as described in U.S. Pat. Nos. 5,445,008 and 6,016,686, incorporated herein by reference. Binding of the specific serum proteins to the antibodies may also be detected via colorimetric or electrochemical-mediated reactions. Other methods that are otherwise known to those of skill in the art are intended to be incorporated here by reference, and may be used in conjunction with the methods described here.

In addition to the measurement of serum lipoproteins in blood, microorganisms, such as Salmonella, *E. coli*, Streptococci, Chlamydia sp. (including *C. trachomatis* and *C. pneumoniae*), Pseudomonas, the HIV virus and other microorganisms, may be detected through antibody, enzyme-mediated detection sensors or any other microorganism detection technology. Of high importance is the monitoring of nosocomial infections in hospital situations. A BIH sensor head may be configured to contain not only vital sign measurement, but also detection of infectious organisms in patient samples. The sensor could be placed in an implantable platform, as above, but also in needles, catheters, respiratory implants or any other implants used in a hospital setting. The sensor could be queried using telemetry technology to continuously monitor the presence of infectious organisms, or directly linked to the BIR through electrical conduction means. The BIH could also be placed in devices or equipment adjacent to the patient for detection of the types of materials being inserted/injected into the patient e.g. Intravenous Pumps and Mechanisms, Respiratory devices, kidney dialysis systems, blood sampling systems and devices, fluid discharge containment devices e.g. bed pans, urine samples, sputum samples, oral sampling devices and systems e.g. cotton swabs, tongue depressors, nasal secretion collection devices e.g. bulbs etc.

The BIH sensor, through a uterine or vaginal implantation device, could also measure the occurrence of uterine or vaginal infections, such as yeast (fungal) infections, Human Papilloma virus, Epstein Barr virus, sexually transmitted agents, or other uterine or vaginal infection. For example, yeast infections could be monitored through the specific detection of agents, such as *Candida albicans*, by antibody-mediated detection, enzyme detection, or other means routinely used in detecting Candida infections. In addition, a second sensor monitoring pH levels may also be incorporated. pH levels are indicative of ideal environments for Candida growth, where a decrease in the acidity of the vaginal environment releases growth inhibition of Candida, and transforms the microbe from a yeast-like to an invasive fungal mycellium form. Early detection of changes in physiological parameters or presence of microbial agents is essential in the prevention and treatment of disease states, including Chronic Fatigue Syndrome.

Use of the HG for Oral Measurements

The mouth is a less commonly employed site of bioparameter measurements but offers a number of significant advantages, including the ability to access body fluids and to monitor exhaled gases. In certain instances, these may serve as alternative measurements to invasive techniques. Using suitable sensors, e.g. a microcantilever MEMS systems, it is possible to measure ketone or aldehyde content within saliva and therefore gauge dietary/nutritional status (e.g. catabolic dietary deficiency) or, for the purpose of breath acceptability in social settings. In other applications, exposure to chemical or biological warfare agents may be assessed by placing within the buccal cavity suitable sensor systems e.g. those for volumetric measurements of oxygen consumption (or partial pressure of oxygen gas, or other gases such as cyanide, Lewisite, or specific toxins or agents. In addition, an oral device could be used to ensure compliance to a therapeutic regimen by analyzing the exhaled gases or fluids within the mouth for markers or other chemical or biological elements that would correlate to the concentration of the therapeutic in the measured subject.

In use, a BIH/CCM system may be affixed to the outside surface of the teeth. Alternatively, a combined BIH/CCM may be placed or positioned between teeth and held in place by dental floss or other similar type device.

Use of the HG for Measurement of Other Biological Parameters

Measurement of other biological parameters that were not contemplated in the preceding examples may be accomplished using the above system by incorporating the appropriate sensor into the HG. For instance, it may be readily envisaged how one skilled in the art might utilize a HG system to augment hearing in select circumstances by placing an acoustic sensor/transmitter BIH assembly within the ear as a cochlear implant and utilize the CCM to transmit data representing audible sounds to the ear. In addition, it will be understood that the present invention may be implemented using other technologies, including direct digital readout of signal output from the sensor platform, and other technologies known to those of skill in the art. All such variations and modifications are intended to be within the scope of the invention claimed by this patent.

We claim:

1. A system for monitoring physiological status of a mammalian subject, comprising:
   a. one or more biointerface heads (BIH), each comprising one or both of a sensor for measuring a physiological parameter and a device for therapeutic compound delivery, at least one of said biointerface heads being implanted subdermally and configured to communicate data and a BIH identifier;
   b. at least one control and communication module (CCM) attached to an external surface of said subject and storing a CCM identifier and which is linked to at least one biointerface head to receive said data and said BIH identifier, wherein said control and communication module processes data from at least one biointerface head;

c. at least one data collection unit (DCU) which receives data and said identifiers from the control and communication module; and d. a remote database management system which receives data from the at least one data collection unit and processes said data.

2. The system of claim 1, wherein said biointerface head is attached to said mammalian subject with at least one adhesive.

3. The system of claim 2, wherein said adhesive contains one or more of the groups comprising: growth factors, adherence molecules, adherence attractants or factors which promote cutaneous wound-healing mechanisms and formation of an epithelial-like structure around a portion of said system.

4. The system of claim 1, wherein said system comprises a transdermal conduit and a biofluid access port, and wherein the transdermal conduit and biofluid access port are coated with a hydrogel material.

5. The system of claims 4, wherein the hycirogel material contains preservatives, anti-inflammatory agents, antibiotics or antimicrobial agents.

6. The system of claims 4, wherein the hydrogel material contains a chemical, compound or molecule for calibration of the sensor.

7. The system of claim 4, wherein the transdermal conduit comprises a fluid material containing preservatives, anti-inflammatory agents, antibiotics or antimicrobial agents.

8. The system of claim 1, wherein said system comprises a chamber which releases one or more therapeutic agents.

9. A system comprising:

a subdermal physiological parameter sensor to measure a physiological parameter of a mammalian subject and to generate measurement information based on the measurements;

a mounting structure that anchors said system to a dermal layer;

a flexible transdermal conduit attached to said mounting structure at or near a first end, wherein said transdermal conduit is in contact with a sensor assembly;

a sensor mounting head, wherein said sensor mounting head is attached to a second end of said transdermal conduit;

a biofluid access port within said sensor mounting head, the biofluid access port further comprising microstructures allowing biofluid flow into the transdermal conduit to contact the sensor assembly and block transmission of external pathogens into a subject;

a control and communication module in data communication with the physiological parameter sensor to receive the measurement information from the physiological parameter sensor, the control and communication module including signal processing circuitry to generate and transmit a first signal based on the measurement information.

10. The system of claim 9, wherein the control and communication module further comprises signal encryption circuitry to encrypt the first signal for transmission.

11. The system of claim 9, wherein said mounting structure is attached to said mammalian subject with at least one adhesive.

12. The system of claim 11, wherein said adhesive contains one or more of the groups comprising: growth factors, adherence molecules, adherence attractants or factors which promote cutaneous wound-healing mechanisms and formation of an epithelial-like structure around the mounting structure.

* * * * *

UNITED STATES PATENT AND TRADEMARK OFFICE
CERTIFICATE OF CORRECTION

PATENT NO. : 7,044,911 B2  Page 1 of 1
APPLICATION NO. : 10/032765
DATED : May 16, 2006
INVENTOR(S) : Drinan et al.

It is certified that error appears in the above-identified patent and that said Letters Patent is hereby corrected as shown below:

In column 29, line 20, in Claim 5, delete "hycirogel" and insert -- hydrogel --, therefore.

Signed and Sealed this

Fourth Day of December, 2007

JON W. DUDAS
*Director of the United States Patent and Trademark Office*